US008207245B2

(12) United States Patent  (10) Patent No.: US 8,207,245 B2
Padsalgikar et al.  (45) Date of Patent: Jun. 26, 2012

(54) GELS

(75) Inventors: Ajay Padsalgikar, Wheelers Hill (AU);
Trang Thanh Nhan, Victoria (AU);
Sriram Venkataramani, Victoria (AU);
Mansour Mehrabi, Victoria (AU);
Mark Bown, Notting Hill (AU)

(73) Assignee: Aortech International plc, Glasgow (GB)

( * ) Notice: Subject to any disclaimer, the term of this patent is extended or adjusted under 35 U.S.C. 154(b) by 166 days.

(21) Appl. No.: 11/663,870

(22) PCT Filed: Sep. 28, 2005

(86) PCT No.: PCT/AU2005/001491
§ 371 (c)(1),
(2), (4) Date: Apr. 14, 2008

(87) PCT Pub. No.: WO2006/034547
PCT Pub. Date: Apr. 6, 2006

(65) Prior Publication Data
US 2008/0293844 A1  Nov. 27, 2008

(30) Foreign Application Priority Data

Sep. 29, 2004 (AU) ................................ 2004905628

(51) Int. Cl.
A61F 2/00 (2006.01)
C08F 283/12 (2006.01)
C08G 18/61 (2006.01)
C08G 77/452 (2006.01)
C08G 77/14 (2006.01)
C08G 77/458 (2006.01)
(52) U.S. Cl. ........ 523/113; 525/453; 525/458; 525/474; 528/10; 528/28; 528/29; 528/33; 528/38
(58) Field of Classification Search .................. 523/113; 522/172; 525/453, 458, 474; 528/10, 28, 528/29, 33, 38
See application file for complete search history.

(56) References Cited

U.S. PATENT DOCUMENTS

| | | | | |
|---|---|---|---|---|
| 3,398,172 | A * | 8/1968 | Noll et al. ............... | 556/420 |
| 5,187,251 | A | 2/1993 | Jachmann et al. | |
| 5,336,797 | A | 8/1994 | McGee et al. | |
| 5,403,912 | A | 4/1995 | Gunatillake et al. | |
| 5,451,617 | A | 9/1995 | Lai et al. | |
| 5,863,627 | A | 1/1999 | Szycher et al. | |
| 6,313,254 | B1 | 11/2001 | Meijs et al. | |
| 2003/0018156 | A1 | 1/2003 | Meijs et al. | |
| 2003/0125498 | A1 | 7/2003 | McCabe et al. | |
| 2004/0054080 | A1 | 3/2004 | Benz et al. | |
| 2006/0223964 | A1 | 10/2006 | Lai et al. | |
| 2010/0029802 | A1 | 2/2010 | Mehrabi et al. | |

FOREIGN PATENT DOCUMENTS

| | | |
|---|---|---|
| AU | 2005289374 | 10/2011 |
| EP | 1081272 A1 | 3/2001 |
| EP | 1251146 A1 | 10/2002 |
| EP | 1251146 B1 | 9/2006 |
| EP | 2007826 A1 | 12/2008 |
| JP | 62224051 | 10/1987 |
| JP | 62224051 A | 10/1987 |
| JP | 2001500912 A | 1/2001 |
| JP | 2001526727 A | 12/2001 |
| JP | 2002509958 A | 4/2002 |
| JP | 2002543231 A | 12/2002 |
| JP | 2003505562 | 2/2003 |
| WO | WO-93/05098 A1 | 3/1993 |
| WO | WO-9305098 A1 | 3/1993 |
| WO | WO-9813405 A1 | 4/1998 |
| WO | WO-9854242 A1 | 12/1998 |
| WO | WO-9950327 A1 | 10/1999 |
| WO | WO-00/64971 A1 | 11/2000 |
| WO | WO-0064971 A1 | 11/2000 |
| WO | WO-0107499 A1 | 2/2001 |
| WO | WO-2004011529 A1 | 2/2004 |
| WO | WO-2004034547 A1 | 4/2004 |
| WO | WO-2004052963 A1 | 6/2004 |
| WO | WO-2004062531 A1 | 7/2004 |
| WO | WO-2005/005517 A2 | 1/2005 |
| WO | WO-2006034547 A1 | 4/2006 |
| WO | WO-2006107899 A1 | 10/2006 |

OTHER PUBLICATIONS

"International Search Report for corresponding PCT Application No. PCT/AU2005/001491", (Jan. 3, 2006), 3 pgs.
"International Application No. PCT/AU2005001491, Search Report", 5.
"European Application Serial No. 05791328.7, Supplementary European Search Report mailed Mar. 4, 2010", 5 pgs.
"International Application Serial No. PCT/AU2005/001491, International Preliminary Report on Patentability completed Dec. 11, 2006", 7 pgs.
"International Application Serial No. PCT/AU2005/001491, Written Opinion dated Jan. 3, 2006", 5 pgs.
"European Application Serial No. 05791328.7, Office Action mailed Feb. 11, 2011", 2 pgs.
Van Bommel, M. J, "The influence of the addition of alkyl-substituted ethoxysilane on the hydrolysiscondensation process of TEOS", Journal of Non-Crystallines Solids 128, (1991), 231-242.
"Application U.S. Appl. No. 12/226,508, Restriction Requirement mailed Aug. 31, 2011", 7 pgs.
"Australian Application Serial No. 2007242052, Office Action mailed Oct. 17, 2011", 2 pgs.
"European Application Serial No. 07718758.1, Office Action mailed Nov. 10, 2011", 3 pgs.
"India Application Serial No. 1026/KOLNP/2007, First Examiner Report mailed Oct. 12, 2010", 2 pgs.

(Continued)

Primary Examiner — Michael Pepitone
(74) Attorney, Agent, or Firm — Schwegman, Lundberg & Woessner, P.A.

(57) ABSTRACT

The present invention relates to silicon-containing biostable gels and processes for their preparation. The gels possess properties which make them useful in the manufacture and repair of biomaterials and medical devices, articles or implants, in particular the manufacture of soft tissue implants such as breast implants and the repair of orthopaedic joints such as spinal discs.

8 Claims, No Drawings

OTHER PUBLICATIONS

"International Application Serial No. PCT/AU2005/001491, International Search Report mailed on Jan. 3, 2006", 3 pg.

"International Application Serial No. PCT/AU2007/000511, International Preliminary Report on Patentability mailed Aug. 22, 2008", 9 pgs.

"International Application Serial No. PCT/AU2007/000511, International Search Report mailed Jun. 28, 2007", 3 pgs.

"International Application Serial No. PCT/AU2007/000511, Response filed Jan. 24, 2008 to Written Opinion mailed Jun. 20, 2007", 6 pgs.

"International Application Serial No. PCT/AU2007/000511, Response filed Apr. 8, 2008 to Written Opinion mailed Jun. 20, 2007", 3 pgs.

"International Application Serial No. PCT/AU2007/000511, Second Written Opinion mailed May 30, 2008", 4 pgs.

"International Application Serial No. PCT/AU2007/000511, Written Opinion mailed Jun. 20, 2007", 6 pgs.

"Japanese Application Serial No. 2007-533824, First Office Action mailed Oct. 18, 2011", 4 pgs.

\* cited by examiner

GELS

RELATED APPLICATIONS

This application is a nationalization under 35 U.S.C. 371 of PCT/AU2005/001491, filed Sep. 28, 2005 and published as WO 2006/034547 A1, on Apr. 6, 2006, which claimed priority under 35 U.S.C. 119 to Australian Application No. 2004905628, filed Sep. 29, 2004; which applications and publication are incorporated herein by reference and made a part hereof.

The present invention relates to silicon-containing biostable gels and processes for their preparation. The gels possess properties which make them useful in the manufacture and repair of biomaterials and medical devices, articles or implants, in particular the manufacture of soft tissue implants such as breast implants and the repair of orthopaedic joints such as spinal discs.

BACKGROUND

Polymer gels are semi-solid systems that respond in a liquid like fashion under certain circumstances but their molecules do not have motion that is independent of each other, hence they behave like solids in other circumstances.

Gels can be synthesised as physical gels where a cross-linked network is swelled by a non reactive liquid. Without the presence of this swelling medium the cross-linked network would be a solid. Silicone gels currently used in breast implants are physical gels where a cross-linked polydimethylsiloxane (PDMS) system is swollen by a non reactive, low molecular weight PDMS. These gels are inherently prone to leakage of the low molecular weight liquid PDMS and contain heavy metal catalysts such as platinum and tin which can leach out of the implant in an in-vivo situation.

Hydrogels are other examples of physical gels, where hydrophilic groups in the cross-linked network can attract water molecules and are swollen by them. In a physical gel the parts by weight of the swelling medium can be as high as 90%. This swelling medium can be extracted out of the gel by most solvents and biological fluids.

There is a need for a gel that mimics the behaviour of a PDMS-based physical gel, but is chemically formulated so as to avoid the complications of a physical gel.

SUMMARY

According to the present invention there is provided a gel comprising at least one silicon-containing biostable polymer having an average functionality in the range of from 2 to 5, preferably from 2.05 to 3.5, more preferably from 2.1 to 3.25.

The biostable polymer is preferably a polyurethane or polyurethane urea.

In one embodiment, the polyurethane or polyurethane urea is the reaction product of:
(a) at least one silicon-containing polyol or polyamine having 1 or more functional groups; and
(b) a polyisocyanate.

In another embodiment the polyurethane or polyurethane urea defined above may also be the reaction product of:
(c) at least one non-silicon containing compound having 1 or more functional groups The present invention also provides a process for preparing the polyurethane polyurethane urea defined above which comprises the step of:
(i) mixing components (a), (b) and (c) (when present) as defined above.

In an alternative embodiment, the process for preparing the polyurethane or polyurethane urea defined above comprises the steps of:
(i) reacting components (a) and (b) as defined above to form a prepolymer having terminally reactive polyisocyanate groups; and
(ii) mixing the prepolymer of step (i) with component (c) (when present) as defined above.

In a further embodiment, the process for preparing the polyurethane or polyurethane urea defined above comprises the steps of:
(i) mixing components (a) and (b) and (c) (when present) as defined above with a photoinitiater; and
(ii) subjecting the mixture to UV radiation.

Some of the silicon-containing polyols (a) defined above are novel and form part of the invention.

Further according to the present invention there is provided a silicon-containing polyol or polyamine of formula (I) or (II):

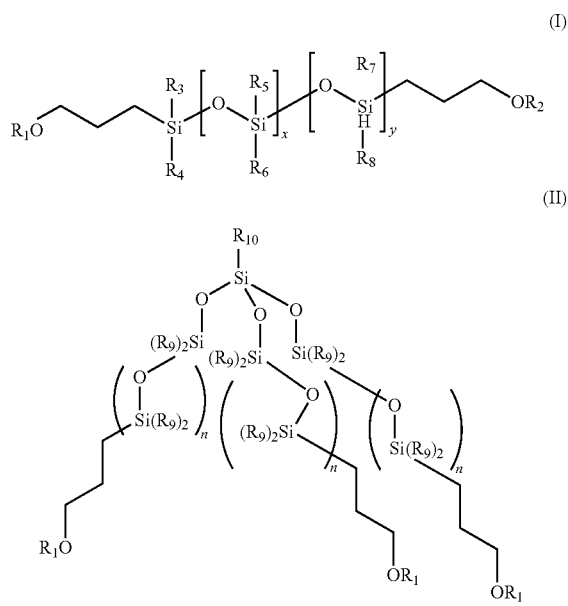

in which $R_1$ and $R_2$ are independently selected from $C_{1-6}$ alkylene optionally substituted with OH or NR'R" in which R' and R" are independently selected from H, $CO_2H$ and $C_{1-6}$ alkyl;

$R_3$ to $R_8$ are independently selected from $C_{1-6}$ alkyl and $C_{1-6}$ alkylene which may be optionally interrupted by O and optionally substituted with OH or NR'R" in which R' and R" are as defined above;

$R_9$ is $C_{1-4}$ alkyl;

$R_{10}$ is optionally substituted $C_{1-4}$ alkyl or

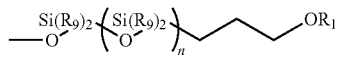

in which $R_1$ and $R_9$ are as defined above;

x is 5 to 30;

y is 1 to 10; and n is 1 to 10.

The present invention further provides a process for the preparation of the silicon-containing polyol of formula (I) or (II) defined above which comprises the steps of:

(i) reacting a compound of formula (A) or (B)

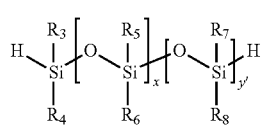
(A)

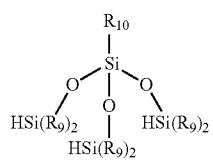
(B)

in which $R_3$ to $R_{10}$ and x are as defined above and y' is 0 to 10. with a compound of formula (C)

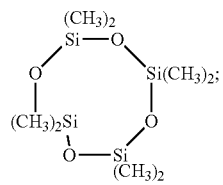
(C)

and (ii) subjecting the product of step (i) to hydrosilation.

The gels of the present invention possess viscoelastic properties and have a natural tissue feel to suit, for example, soft tissue implant gel applications such as breast implants. These gels also have a low level of extractables preferably less than 35%, more preferably less than 30%, most preferably less than 21% based on the total weight of the gel.

Thus, the present invention also provides a biomaterial, device, article or implant which is wholly or partly composed of the gels defined above.

The present invention further provides a filler material for a medical implant which comprises the gel defined above.

DETAILED DESCRIPTION

The gel of the present invention which comprises at least one silicon containing biostable polymer is a chemical gel. When a cross-linked network is formulated such that the reactive groups are in a perfect balance then, during the course of the reaction, the network begins to vitrify and ends up being a hard solid. If the reaction is not allowed to go to completion by creating an imbalance in the reactive groups, then an off-stoichiometric system occurs which is capable of gelation. Thus, one reactive group is in excess and remains incompletely reacted. This excess amount acts similar to the non-reactive swelling medium in physical gels. However, usually lower amounts of unreacted material, in comparison to the swelling agents, can be formulated to achieve a similar effect to a physical gel and that, in turn, implies lower extractable species. The level of extractables in the gel of the present invention is preferably less than 35%, more preferably less than 30%, most preferably less than 21% based on the total weight of the gel.

The term "extractables" refers to the unreacted portion of the gel which is generally fluid and free to migrate out of the gel at body temperature of 38° C. and more specifically, refers to the unreacted fluid portion of a gel which is extracted by organic solvents at temperatures in the range from 20° C. to 40° C.

The term "biostable" refers to the stability of the polymer when in contact with cells and/or bodily fluids of living animals or humans.

The term "average functionality" of a polymerisation system refers to the average number of functional groups per monomer for all types of monomer molecules and is defined by the following formula:

in which $$f_{avg} = \frac{\sum_i n_i f_i}{\sum_i n_i}$$

$n_i$ is number of molecules of monomer i with functionality groups $f_i$.

Preferably, the average functionality of the gel is in the range of from 2.05 to 3.5, more preferably from 2.1 to 3.25.

The biostable polymer may be a polyurethane, polyurethane urea, polyolefin, polyester, polytetrafluoroethylene or polymethacrylate such as poly(methylmethacrylate).

Preferably the biostable polymer is a polyurethane or polyurethane urea.

The polyurethane or polyurethane urea may be formed from a silicon-containing polyol or polyamine having 1 or more functional groups (a), a polyisocyanate (b) and optionally a non-silicon containing compound having 1 or more functional groups (c).

The functional groups of components (a) and (c) may be any types of groups which can react with isocyanate and are preferably selected from OH, NR'R" in which R' and R" are the same or different and selected from H, $CO_2H$ and $C_{1-6}$ alkyl, preferably H and $C_{1-4}$ alkyl or are groups capable of activation by free radical initiation such as double or triple bonds.

The silicon-containing polyol or polyamine (a) can have 1 or more functional groups provided that the average functionality of the biostable polymer is in the range from 1 to 5.

Suitable silicon-containing polyols or polyamines (a) include compounds of the formula (I) or (II) defined above, polysiloxanes or silicon-containing polycarbonates.

Representative examples of compounds of the formula (I) are as follows:
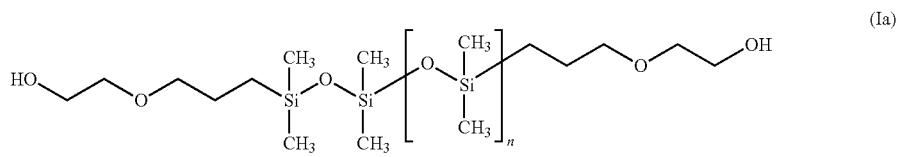
(Ia)
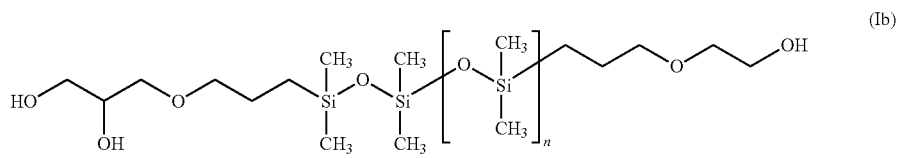
(Ib)
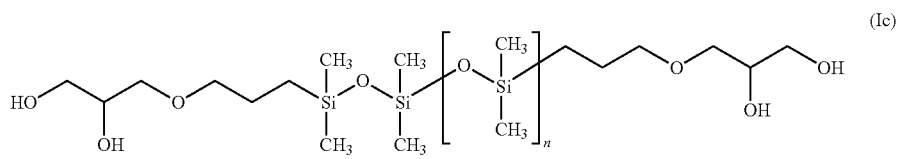
(Ic)
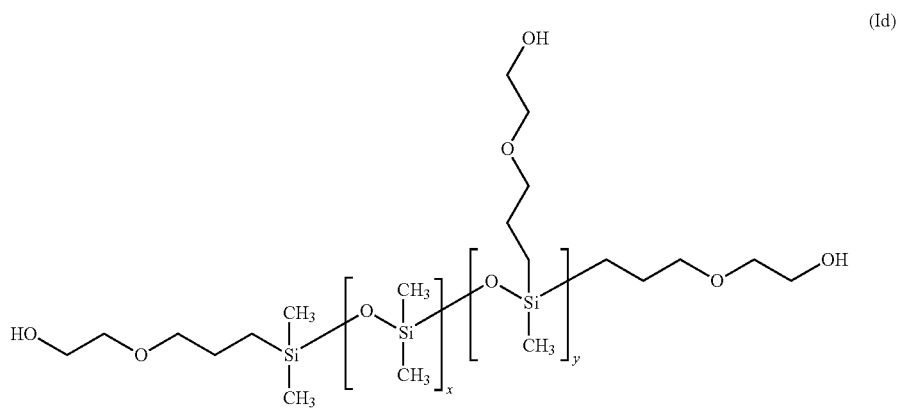
(Id)
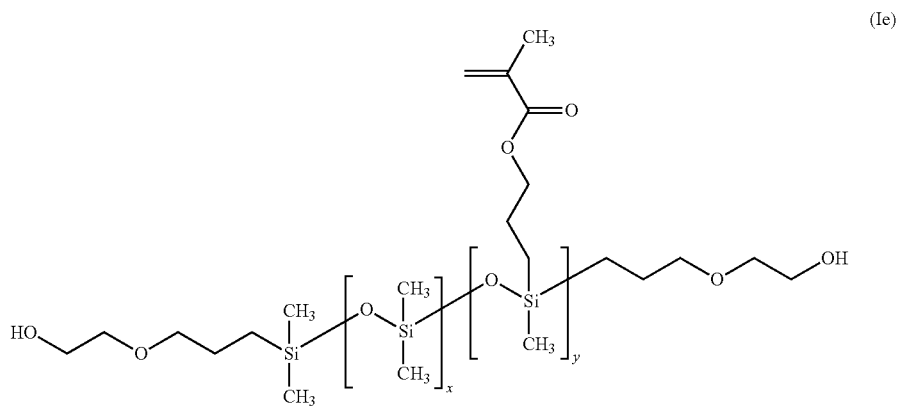
(Ie)
The molecular weight of the compounds of formula (I) is preferably from 400 to 5000. It will be understood that the molecular weight values referred to herein are "number average molecular weights".

Representative examples of compounds of the formula (II) are as follows:

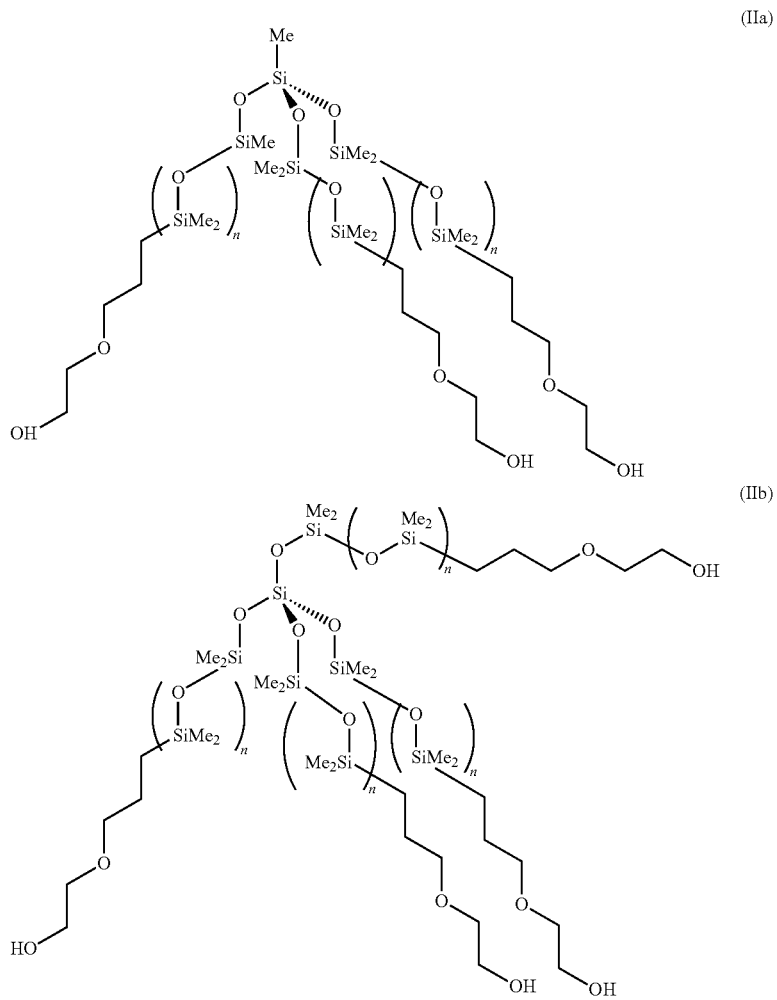

The molecular weight of the compounds of formula (II) is preferably from 1000 to 5000.

The polysiloxane may be hydroxy or amine terminated. Suitable polysiloxane macrodiols or macrodiamines may be represented by the formula (III):

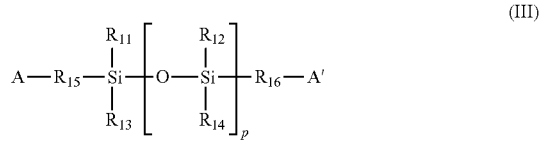

in which

A and A' are OH or NHR wherein R is H or an optionally substituted straight chain, branched or cyclic, saturated or unsaturated hydrocarbon radical, preferably $C_{1-6}$ alkyl, more preferably $C_{1-4}$ alkyl;

$R_{11}$, $R_{12}$, $R_{13}$ and $R_{14}$ are the same or different and selected from hydrogen or an optionally substituted straight chain, branched or cyclic, saturated or unsaturated hydrocarbon radical;

$R_{15}$ and $R_{16}$ are the same or different and selected from an optionally substituted straight chain, branched or cyclic alkylene, alkenylene, alkynylene or heterocyclic divalent radical; and p is an integer of 1 or greater.

Preferred polysiloxanes are polysiloxane macrodiols which are polymers of the formula (III) wherein A and A' are hydroxy.

A preferred polysiloxane is PDMS which is a compound of formula (III) in which A and A' are hydroxyl, $R_{11}$ to $R_{14}$ are methyl and $R_{15}$ and $R_{16}$ are as defined above. Preferably $R_{15}$ and $R_{16}$ are the same or different and selected from propylene, butylene, pentylene, hexylene, ethoxypropyl ($-CH_2CH_2OCH_2CH_2CH_2-$), propoxypropyl and butoxypropyl.

Other silicon-containing diols of the formula (III) are 1,3-bis(4-hydroxybutyl)tetramethyl disiloxane (BHTD) (compound of formula (III) in which A and A' are OH, $R_{11}$, $R_{12}$, $R_{13}$ and $R_{14}$ are methyl, $R_{15}$ and $R_{16}$ are butyl and $R_{17}$ is O), 1,4-bis(3-hydroxypropyl)tetramethyl disilylethylene (compound of formula (III) in which A and A' are OH, $R_1$, $R_{12}$, $R_{13}$ and $R_{14}$ are methyl, $R_{15}$ and $R_{16}$ are propyl and $R_{17}$ is ethylene) and 1-4-bis(3-hydroxypropyl)tetramethyl disiloxane, more preferably BHTD.

The polysiloxanes may be obtained as commercially available products such as X-22-160AS from Shin Etsu in Japan or prepared according to known procedures. The preferred molecular weight range of the polysiloxane macrodiol is 200 to 6000, more preferably from 200 to 5000.

Other preferred polysiloxanes are polysiloxane macrodiamines which are polymers of the formula (III) wherein A is $NH_2$, such as, for example, amino-terminated PDMS.

Suitable silicon-containing polycarbonates include those described in International Patent Publication No. WO 98/54242, the entire content of which is incorporated herein by reference.

A preferred silicon-containing polycarbonate has the formula (IV):

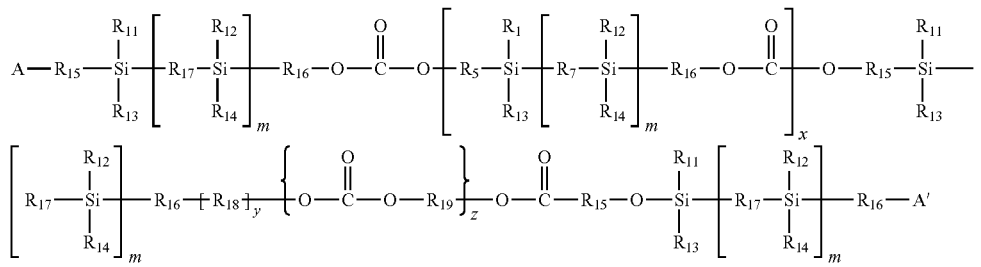

in which $R_{11}$, $R_{12}$, $R_{13}$, $R_{14}$ and $R_{15}$ are as defined in formula (III) above;

$R_{16}$ is an optionally substituted straight chain, branched or cyclic alkylene, alkenylene, alkynylene or heterocyclic divalent radical;

$R_{17}$ is a divalent linking group, preferably O, S or $NR_{18}$;

$R_{18}$ and $R_{19}$ are same or different and selected from hydrogen or an optionally substituted straight chain, branched or cyclic, saturated or unsaturated hydrocarbon divalent radical;

A and A' are as defined in formula (III) above;

m, y and z are integers of 0 or more; and x is an integer of 0 or more.

Preferably z is an integer of 0 to 50 and x is an integer of 1 to 50. Suitable values for m include 0 to 20, more preferably 0 to 10. Preferred values for y are 0 to 10, more preferably 0 to 2.

A preferred silicon-containing polycarbonate is a compound of the formula (IV) in which A and A' are hydroxyl.

Particularly preferred silicon-containing polycarbonate macrodiols are compounds of the formula (IV) in which A and A' are hydroxyl, $R_{11}$, $R_{12}$, $R_{13}$ and $R_{14}$ are methyl, $R_{18}$ is ethyl, $R_{19}$ is hexyl, $R_{15}$ and $R_{16}$ are propyl or $R_{14}$ butyl and $R_{17}$ is 0 or —$CH_2$—$CH_2$—, more preferably $R_5$ and $R_{16}$ are propyl when $R_{17}$ is 0 and $R_{15}$ and $R_{16}$ are butyl when $R_{17}$ is —$CH_2$—$CH_2$—. The preferred molecular weight range of the silicon-based polycarbonate macrodiol is from 400 to 5000, more preferably from 400 to 2000.

The term "polyisocyanate" refers to di or higher isocyanates such as polymeric 4,4'-diphenylmethane diisocyanate (MDI). The polyisocyanate is preferably a diisocyanate which may be aliphatic or aromatic diisocyanates such as, for example MDI, methylene biscyclohexyl diisocyanate ($H_{12}$MDI), p-phenylene diisocyanate (p-PDI), trans-cyclohexane-1,4-diisocyanate (CHDI), 1,6-diisocyanatohexane (DICH), 1,5-diisocyanatonaphthalene (NDI), para-tetramethylxylenediisocyanate (p-TMXDI), meta-tetramethylxylene diisocyanate (m-TMXDI), 2,4-toluene diisocyanate (2,4-TDI) isomers or mixtures thereof or isophorone diisocyanate (IPDI). MDI is particularly preferred.

The non-silicon containing compound having 1 or more functional groups (c) may be a polyether, polycarbonate, polyalkylene or $C_{1-6}$ alkane.

The polyethers and polycarbonates may contain hydroxy or amine functional groups.

Suitable polyether macrodiols and macrodiamines include those represented by the formula (V)

$$A\text{-}[(CH_2)_m\text{—}O]_n\text{-}A' \quad (V)$$

in which

A and A' are as defined in formula (III) above OH or NHR wherein R is H or an optionally substituted straight chain, branched or cyclic, saturated or unsaturated hydrocarbon radical, preferably $C_{1-6}$ alkyl, more preferably $C_{1-4}$ alkyl;

m is an integer of 4 or more, preferably 5 to 18; and n is an integer of 2 to 50.

Polyether macrodiols of formula (V) wherein m is 5 or higher such as polyhexamethylene oxide (PHMO), polyheptamethylene oxide, polyoctamethylene oxide (POMO) and polydecamethylene oxide (PDMO) are preferred over the conventional polytetramethylene oxide (PTMO). The more preferred macrodiols and their preparation are described in Gunatillake et al[3] and U.S. Pat. No. 5,403,912. Polyethers such as PHMO described in these references are particularly useful as they are more hydrophobic than PTMO and more compatible with polysiloxane macrodiols.

Examples of tri- and tetra-functional polyethers include Voranol which is a polyether triol resulting from a base catalysed reaction of glycerol and propylene oxide and N,N,N'-tri(2-hydroxypropyl)-N'-hydroxyethyl ethylene diamine (Poly Q), respectively.

The preferred molecular weight range of the polyether is from 200 to 5000, more preferably from 200 to 2000.

Suitable polycarbonate macrodiols include poly(alkylene carbonates) such as poly(hexamethylene carbonate) and poly(decamethylene carbonate); polycarbonates prepared by reacting alkylene carbonate with alkanediols for example 1,4-butanediol, 1,10-decanediol (DD), 1,6-hexanediol (HD) and/or 2,2-diethyl 1,3-propanediol (DEPD); and silicon based polycarbonates prepared by reacting alkylene carbonate with 1,3-bis(4-hydroxybutyl)-1,1,3,3-tetramethyldisiloxane (BHTD) and/or alkanediols.

It will be appreciated when both the polyether and polycarbonate macrodiols are present, they may be in the form of a mixture or a copolymer. An example of a suitable copolymer is a copoly(ether carbonate) macrodiol represented by the formula (VI)

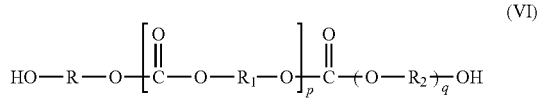

wherein

R$_1$ and R$_2$ are the same or different and selected from an optionally substituted straight chain, branched or cyclic alkylene, alkenylene, alkynylene or heterocyclic divalent radical; and p and q are integers of 1 to 20.

Although the compound of formula (VI) above indicates blocks of carbonate and ether groups, it will be understood that they also could be distributed randomly in the main structure.

Examples of C$_{1-6}$ alkanes having 1 or more functional groups include methane diol, butane diol or hexane diol.

In one embodiment, components (a) and (c) may be a combination of silicon-containing polyols and non-silicon containing polyols having different amounts of functional groups. For example, component (c) may contain a combination of a tri-functional polyether and a tetra-functional polyether.

The components (a), (b) and (c) are preferably mixed so that the NCO/OH or NH$_2$ ratio is less than 1, more preferably from 0.4 to 0.7 so as to provide the appropriate rheological response.

In a particularly preferred embodiment suitable for breast implant applications, the gel is a polyurethane urea which is the reaction product of:
  (a) silicon-containing polyols having 2 to 4 functional groups, namely PDMS (MW 1000) and one or more compounds of the formulae (Id) (MW 1210), (IIa) (MW 1150), (Ic) (MW 430) and (IIb) (MW 1520); and
  (b) a diisocyanate, namely MDI.

The term "alkylene" is a divalent radical equivalent of the term "alkyl". The two bonds connecting the alkylene to the adjacent groups may come from the same carbon atom or difference carbon atoms in the divalent radical.

The "hydrocarbon radical" may include alkyl, alkenyl, alkynyl, aryl or heterocyclyl radicals.

The term "alkyl" denotes straight chain, branched or mono- or poly-cyclic alkyl, preferably C$_{1-12}$ alkyl or cycloalkyl, more preferably C$_{1-6}$ alkyl, most preferably C$_{1-4}$ alkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethylpropyl, pentyl, neopentyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1,2-pentylheptyl and the like. Examples of cyclic alkyl include cyclopropyl, cyclobutyl, cyclopentyl, cyclohexyl, cycloheptyl, cyclooctyl, cyclononyl, cyclodecyl and the like.

The term "alkenyl" denotes groups formed from straight chain, branched or mono- or poly-cyclic hydrocarbon groups having at least one double bond, preferably C$_{2-12}$ alkenyl, more preferably C$_{2-6}$ alkenyl. The alkenyl group may have E or Z stereochemistry where applicable. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl, 1,3,5,7-(cyclooctatetraenyl) and the like.

The term "alkynyl" denotes groups formed from straight chain, branched, or mono- or poly-cyclic hydrocarbon groups having at least one triple bond. Examples of alkynyl include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl, 5-hexynyl, 10-undecynyl, 4-ethyl-1-octyn-3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl, 3-octadecynyl and the like.

The term "aryl" denotes single, polynuclear, conjugated and fused residues of aromatic hydrocarbons. Examples of aryl include phenyl, biphenyl, terphenyl, quaterphenyl, phenoxyphenyl, naphthyl, tetrahydronaphthyl, anthracenyl, dihydroanthracenyl, benzanthracenyl, dibenzanthracenyl, phenanthrenyl and the like.

The term "heterocyclyl" denotes mono- or poly-cyclic heterocyclyl groups containing at least one heteroatom selected from nitrogen, sulphur and oxygen. Suitable heterocyclyl groups include N-containing heterocyclic groups, such as, unsaturated 3 to 6 membered heteromonocyclic groups containing 1 to 4 nitrogen atoms, for example, pyrrolyl, pyrrolinyl, imidazolyl, pyrazolyl, pyridyl, pyrimidinyl, pyrazinyl, pyridazinyl, triazolyl or tetrazolyl; saturated 3 to 6 membered heteromonocyclic groups containing 1 to 4 nitrogen atoms, such as pyrrolidinyl, imidazolidinyl, piperidino or piperazinyl; unsaturated condensed heterocyclic groups containing 1 to 5 nitrogen atoms, such as, indolyl, isoindolyl, indolizinyl, benzimidazolyl, quinolyl, isoquinolyl, indazolyl, benzotriazolyl or tetrazolopyridazinyl; unsaturated 3 to 6-membered heteromonocyclic group containing an oxygen atom, such as, pyranyl or furyl; unsaturated 3 to 6-membered heteromonocyclic group containing 1 to 2 sulphur atoms, such as, thienyl; unsaturated 3 to 6-membered heteromonocyclic group containing 1 to 2 oxygen atoms and 1 to 3 nitrogen atoms, such as, oxazolyl, isoazolyl or oxadiazolyl; saturated 3 to 6-membered heteromonocyclic group containing 1 to 2 oxygen atoms and 1 to 3 nitrogen atoms, such as, morpholinyl; unsaturated condensed heterocyclic group containing 1 to 2 oxygen atoms and 1 to 3 nitrogen atoms, such as, benzoxazolyl or benzoxadiazolyl; unsaturated 3 to 6-membered heteromonocyclic group containing 1 to 2 sulphur atoms and 1 to 3 nitrogen atoms, such as thiazolyl or thiadiazolyl; saturated 3 to 6-membered heteromonocyclic group containing 1 to 2 sulphur atoms and 1 to 3 nitrogen atoms, such as, thiadiazolyl; and unsaturated condensed heterocyclic group containing 1 to 2 sulphur atoms and 1 to 3 nitrogen atoms, such as benzothiazolyl or benzothiadiazolyl.

In this specification, "optionally substituted" means that a group may or may not be further substituted with one or more groups selected from oxygen, nitrogen, sulphur, alkyl, alkenyl, alkynyl, aryl, halo, haloalkyl, haloalkenyl, haloalkynyl, haloaryl, hydroxy, alkoxy, alkenyloxy, alkynyloxy, aryloxy, carboxy, benzyloxy, haloalkoxy, haloalkenyloxy, haloalkynyloxy, haloaryloxy, nitro, nitroalkyl, nitroalkenyl, nitroalkynyl, nitroaryl, nitroheterocyclyl, azido, amino, alkylamino, alkenylamino, alkynylamino, arylamino, benzylamino, acyl, alkenylacyl, alkynylacyl, arylacyl, acylamino, acyloxy, aldehydro, alkylsulphonyl, arylsulphonyl, alkylsulphonylamino, arylsulphonylamino, alkylsulphonyloxy, arylsulphonyloxy, heterocyclyl, heterocycloxy, heterocyclylamino, haloheterocyclyl, alkylsulphenyl, arylsulphenyl, carboalkoxy, carboaryloxy, mercapto, alkylthio, arylthio, acylthio and the like The polyurethanes of the present invention may be prepared by any technique familiar to those skilled in the manufacture of polyurethanes. These include one or two-step procedures. The polymerisation can be carried out in conventional apparatus or within the confines of a reactive injection moulding or mixing machines.

In a one-step procedure the appropriate amount of components (a), (b) and (c) if present are mixed. The mixture is then cured by heating in an oven to about 70° C.

In an alternative one-step procedure, components (a) and (c) (when present) are added to component (b) slowly. It has also been found that the order of addition of components (a) and (c) may effect the properties of the gel.

The polyurethanes can also be prepared by a two-step procedure where a prepolymer having terminally reactive polyisocyanate groups is prepared by reacting components (a) and (b). The prepolymer is then reacted with the component (c) if present.

The polyurethanes may be further prepared by UV curing which involves the addition of a photoinitiator to components (a), (b) and (c) followed by the application of UV radiation.

If desired, conventional polyurethane processing additives such as catalysts for example dibutyl tin dilaurate (DBTD), stannous oxide (SO), 1,8-diazabicyclo[5,4,0]undec-7-ene (DABU), 1,3-diacetoxy-1,1,3,3-tetrabutyldistannoxane (DTDS), 1,4-diaza-(2,2,2)-bicyclooctane (DABCO), N,N,N',N'-tetramethylbutanediamine (TMBD) and dimethyltin dilaurate (DMTD); antioxidants for example Irganox®; radical inhibitors for example trisnonylphenyl phosphite (TNPP); stabilisers; lubricants for example Irgawax®; dyes; pigments; inorganic and/or organic fillers; and reinforcing materials; and initiators such as photoinitiators, for example, Iragacure 819 can be incorporated into the biostable polymer during preparation. Such additives are preferably added in step (i) of the processes of the present invention up to 10% based on the total weight of gel, preferably up to 5%, more preferably 2% or less.

The polyurethanes of the present invention are particularly useful in preparing biomaterials and medical devices, articles or implants.

The term "biomaterial" refers to a material which is used in situations where it comes into contact with the cells and/or bodily fluids of living animals or humans.

The medical devices, articles or implants may include soft tissue implants designed to replace and augment tissues including breast tissue, testicular tissue, cartilage, muscle and any connective tissue apart from teeth and bone; orthopaedic joints or parts thereof including spinal discs and small joints; bone suture anchors; reconstructive facial surgery; controlled drug release devices; components in key hole surgery; biosensors; tools and accessories for insertion of medical devices, infusion and flow control devices; and urethral, neurological or vascular bulking agents.

In the description of the invention, except where the context requires otherwise due to express language or necessary implication, the words "comprise" or variations such as "comprises" or "comprising" are used in an inclusive sense, i.e. to specify the presence of the stated features but not to preclude the presence or addition of further features in various embodiments of the invention.

EXAMPLES

The invention will now be described with reference to the following non-limiting examples.

Physical Property Tests

Biological Stability: The biological stability of the gels is achieved by the incorporation of large amount of silicon.

Rheology: Both the natural feel and the form stability can be related to rheological factors. A good creep-recovery performance describes the feel or the elasticity. The parameters of storage modulus (G') and loss modulus (G") as measured in frequency sweep measurement on a rheometer describe the form stability. G'>G" at low frequencies ($0.01$ s$^{-1}$ to $1$ s$^{-1}$) implies form stability.

Procedure for Creep Recovery & Frequency Sweep Analysis

The Creep Recovery is tested using Haake RheoStress 1 Rheometer. After the initialisation process under compressed air atmosphere, the parallel plates are subjected to zero point measurement. The sample is loaded and the gap position set. The excess sample is trimmed and is ready for the experiment.

The creep recovery analysis is carried out at 37° C. The sample is thermostated for 300 s before the actual experiment starts to ensure temperature equilibrium. The experiment is carried at a force of 10 Pa for a duration of 60 s and from the plot of J (1/Pa, compliance) Vs t(s), the creep recovery results can be obtained.

For frequency sweep measurement, after trimming the sample, the experiment was conducted at 37° C., with similar temperature equilibrating conditions. It is carried out in the frequency range of 0.01 Hz to 10 Hz. The frequency sweep provides about the structural conditions of the sample. It is possible to distinguish between a particle solution, an entangled solution (paste) and a three dimensional network (gel) simply by the shape of G', G" (Pa) and $\eta^*$ (Pa s) Vs f (Hz) curves.

Extractables: The extractables in hexane as measured in the Soxhlet extraction technique over 24 hours shows an average value of around 50% for the silicone gels.

Extraction Procedure

The extraction procedure involved five pieces of apparatus: condenser, soxhlet extractor tube, extraction thimble, 250 mL round-bottom flask and a heating mantle. The procedure was carried out as follow:

Accurately weighed the 250 mL round bottom (R.B.) flask.
Poured approximately 160 mL of Hexane into the R.B. flask
Placed a known amount of gel sample into the thimble and the thimble was placed in the soxhlet extractor tube.
The R.B. flask was adapted to the lower end of the soxhlet extractor tube and the condenser was adapted the top end of the tube.
The gel sample was allowed to reflux in Hexane for 22 hours.
At the end of the extraction period, the extractables in Hexane were collected in the R.B. flask.
Hexane was removed using rotary evaporator.
The R.B. flask containing the extractable residue was accurately weighed
The amount of extractable residue was calculated from the weight of the gel used for extraction.
The results were report as % weight loss.

Basic Strategy

The approaches used in the formulation of gels involve initiation of cross-linking by the use of various functionalities of the reactants including unsaturated or double bonds in the PDMS molecule and then making the double bond reactive by using a ultraviolet light source or other techniques.

Reactants Used for Gel Synthesis

The reactants used for synthesising the gels include a di-isocyanate in the form of MDI and different hydroxyl terminated polyols of functionalities varying from 1 to 4. The reactants are set out in Table 1 below:

TABLE 1

| Isocyanate | Methylene diphenylene isocyanate (MDI) |
|---|---|
| Silicon containing bi-functional macro-diol | bis(6-hydroxyethoxypropyl) polydimethylsiloxane (PDMS) of number average molecular weight (Mn) between 900-2100 |
| Tri-functional Polyols | A mixture of silicon containing polyols of different functionalities with an effective functionality of 3 |
| | A silicon containing polyol having an actual functionality of 3 |
| | Tri-functional polyether polyol - Voranol 2070 (Dow Chemicals) of Mn 700 |
| Tetra functional | A mixture of silicon containing polyols of different functionalites with an effective functionality of 4 |
| | A silicon containing polyol having an actual functionality of 4 |
| | N,N,N'-tri(2-hydroxy propyl)-N'-hydroxy ethyl ethylene diamine, Poly Q 40 800, from Arch Chemicals Inc. of Mn 237 |

Some of the above reactants are available commercially, however, the silicon-containing multifunctional polyols are not available commercially have been synthesised in Examples A to E below.

Example A

This example illustrates the preparation of a statistical (1:2:1) mixture of α,ω-bis(hydroxyethoxypropyl) polydimethylsiloxane (Ia), α-(hydroxyethoxypropyl)-ω-(6,7-dihydroxyethoxypropyl) polydimethylsiloxane (Ib), and α,ω-bis(6,7-dihydroxyethoxypropyl) polydimethylsiloxane (Ic).

276.00 g of octamethylcyclotetrasiloxane ($D_4$) and 125.00 g of 1,1,3,3-tetramethyldisiloxane (TMDS) were mixed in a glass bottle containing a magnetic stirrer bar. 0.71 g of trifluoromethanesulfonic acid was added to the mixture and the bottle sealed with an air tight cap. The mixture was stirred vigorously for 6 hours at room temperature after which 20 g of sodium carbonate was added. The bottle was resealed and stirred over night, after which the sodium carbonate was filtered off to give 388.58 g of hydride terminated PDMS intermediate.

In a three-neck 1 L round bottomed flask equipped with a water cooled condensed equipped with a silica gel drying tube, a 250-mL pressure compensating dropping funnel, and a thermometer were placed 310 g of the hydride terminated PDMS intermediate given above and 300 mL of dry toluene. The mixture was heated, whilst stirring, to 60° C. 2 mL of a toluene solution of Karstedt's catalyst (containing $36.8 \times 10^{-6}$ moles Pt/mL) was added to the mixture. A mixture of 76.64 g of 2-allyloxyethanol and 95.29 g of 3-allyloxy-1,2-propanediol was added drop wise to the mixture from the dropping funnel. The addition was made over a 30 minute period during which time the temperature of the mixture rose to 116° C. after which the reaction mixture was maintained at 80° C. for 18 hours. Silanic hydrogen content was checked by infrared spectroscopy. When no trace was detectable the reaction was considered to be complete. The reaction mixture was allowed to cool to room temperature and treated with 15 g of activated carbon for 18 hours whilst stirring. The reaction mixture was filtered through celite to remove the carbon. The toluene was removed by rotary evaporator at 80° C. under a reduced pressure of 20 torr. The mixture was transferred to a kugelrohr distillation apparatus and stripped of low molecular weight species at 130° C. under a reduced of $1 \times 10^{-3}$ torr to give 338.73 g of the statistical (1:2:1) mixture of α,ω-bis(hydroxyethoxypropyl) polydimethylsiloxane (Ia), α-(hydroxyethoxypropyl)-ω-(6,7-dihydroxyethoxypropyl) polydimethylsiloxane (Ib), and α,ω-bis(6,7-dihydroxyethoxypropyl) polydimethylsiloxane (Ic) as a colourless oil (n=4.893, MW 767).

Example B

This example illustrates the preparation of hydroxyethoxypropyl terminated 9.09%-(hydroxyethoxypropyl methyl siloxane)(dimethyl siloxane) copolymer (Id).

296.64 g of $D_4$, 30.67 g of 1,3,5,7-tetramethylcyclotetrasiloxane, and 67.17 g of TMDS were mixed in a glass bottle containing a magnetic stirrer bar. 0.61 g of trifluoromethanesulfonic acid was added to the mixture and the bottle sealed with an air tight cap. The mixture was stirred vigorously for 18 hours at room temperature after which 10 g of sodium carbonate was added. The bottle was resealed and stirred for 6 hours, after which the sodium carbonate was filtered off to give 384.50 g of hydride terminated (methylhydrosiloxane)(dimethylsiloxane) copolymer intermediate.

In a three-neck 1 L round bottomed flask equipped with a water cooled condensed equipped with a silica gel drying tube, a 250-mL pressure compensating dropping funnel, and a thermometer were placed 384.50 g of the hydride terminated poly(methylhydrosiloxane)(dimethylsiloxane) copolymer given above and 200 mL of dry toluene. The mixture was heated, whilst stirring, to 60° C. 0.6 mL of a toluene solution of Karstedt's catalyst (containing $36.8 \times 10^{-6}$ moles Pt/mL) was added to the mixture. 203.75 g of 2-allyloxyethanol was added drop wise to the mixture from the dropping funnel. The addition was made over a 30 minute period during which time the temperature of the mixture rose to 114° C. after which the reaction mixture was maintained at 70° C. for 1 hour. Silanic hydrogen content was checked by infrared spectroscopy. When no trace was detectable the reaction was considered to be complete. The reaction mixture was allowed to cool to room temperature and treated with 20 g of activated carbon for 18 hours whilst stirring. The reaction mixture was filtered through celite to remove the carbon. The toluene was removed by rotary evaporator at 80° C. under a reduced pressure of 20 torr. The mixture was transferred to a kugelrohr distillation apparatus and stripped of low molecular weight species at 100° C. under a reduced of $1 \times 10^{-1}$ torr to give 484.50 g of hydroxyethoxypropyl terminated 9.09% -(hydroxyethoxypropyl methyl siloxane)(dimethyl siloxane) copolymer (Id) as a colourless oil (x=9.53, y=1.29, MW 1189).

Example C

This example illustrates the preparation of α,α',α''-(methylsilylidyne)tris-[ω[(hydroxyethoxypropyldimethylsilyl) oxy]poly(dimethylsilyene)]](9Cl) (IIa).

282.38 g of $D_4$ and 170.48 g of methyltris (dimethylsiloxy) silane were mixed in a glass bottle containing a magnetic stirrer bar. 0.59 g of trifluoromethanesulfonic acid was added to the mixture and the bottle sealed with an air tight cap. The mixture was stirred vigorously for 7 hours at room temperature after which 10 g of sodium carbonate was added. The bottle was resealed and stirred overnight, after which the sodium carbonate was filtered off to give 431.10 g of hydride terminated α,α',α''-(methylsilylidyne)tris-[ω[(dimethylhydrosilyl) oxy]poly(dimethylsilyene)]](9Cl) intermediate.

In a three-neck 1 L round bottomed flask equipped with a water cooled condensed equipped with a silica gel drying tube, a 250-mL pressure compensating dropping funnel, and a thermometer were placed 431.10 g of the α,α',α''-(methylsilylidyne) tris-[ω[(dimethylhydrosilyl) oxy]poly(dimethylsilyene)]](9Cl) intermediate given above and 250 mL of dry toluene. The mixture was heated, whilst stirring, to 70° C. 0.5 mL of a toluene solution of Karstedt's catalyst (containing 0.1 mmoles Pt/mL) was added to the mixture. 210.37 g of 2-allyloxyethanol was added drop wise to the mixture from the dropping funnel. The addition was made over a 45 minute period during which time the temperature of the mixture rose to 95° C. after which the reaction mixture was maintained at 70° C. for 1 hour. Silanic hydrogen content was checked by infrared spectroscopy. When no trace was detectable the reaction was considered to be complete. The reaction mixture was allowed to cool to room temperature and treated with 20 g of activated carbon for 18 hours whilst stirring. The reaction mixture was filtered through celite to remove the carbon. The toluene was removed by rotary evaporator at 80° C. under a reduced pressure of 20 torr. The pale yellow product was treated with 10 g of activated carbon for 3 days to remove the residual colour. The oil was filtered through celite to remove the carbon and then transferred to a kugelrohr distillation apparatus and stripped of low molecular weight species at 140° C. under a reduced of $1 \times 10^{-1}$ torr to give 526.25 g α,α',α''-(methylsilylidyne)tris-[ω[(hydroxyethoxypropyldimethylsilyl)oxy]poly (dimethylsilyene)]](9Cl) (IIa) as a colourless oil (n=1.97, MW 1021).

Example D

This example illustrates the preparation of α,α',α'',α'''-tetrakis-[ω[(hydroxyethoxypropyldimethylsilyl) oxy]poly (dimethylsilyene)]]silane(9Cl) (IIb).

33.80 g of $D_4$ and 75.00 g of tetrakis(dimethylsiloxy) silane were mixed in a glass bottle containing a magnetic stirrer bar. 0.128 g of trifluoromethanesulfonic acid was added to the mixture and the bottle sealed with an air tight cap. The mixture was stirred vigorously for 4 days at room temperature after which 10 g of sodium carbonate was added. The bottle was resealed and stirred for 6 hours, after which the sodium carbonate was filtered off to give 91.92 g of hydride terminated tetrakis (polydimethylsiloxane) silane intermediate.

In a three-neck 1 L round bottomed flask equipped with a water cooled condensed equipped with a silica gel drying tube, a 250-mL pressure compensating dropping funnel, and a thermometer were placed 91.92 g of the hydride terminated methyltris(polydimethylsiloxane)silane intermediate given above and 100 mL of dry toluene. The mixture was heated, whilst stirring, to 60° C. 0.5 mL of a toluene solution of Karstedt's catalyst (containing 0.1 mmoles Pt/mL) was added to the mixture. 98.42 g of 2-allyloxyethanol was added drop wise to the mixture from the dropping funnel. The addition was made over a 30 minute period during which time the temperature of the mixture rose to 104° C. after which the reaction mixture was maintained at 80° C. for 1 hour. Silanic hydrogen content was checked by infrared spectroscopy. When no trace was detectable the reaction was considered to be complete. The reaction mixture was allowed to cool to room temperature and treated with 10 g of activated carbon for 18 hours whilst stirring. The reaction mixture was filtered through celite to remove the carbon. The toluene was removed by rotary evaporator at 80° C. under a reduced pressure of 20 torr and then transferred to a kugelrohr distillation apparatus and stripped of low molecular weight species at 120° C. under a reduced of $1 \times 10^{-1}$ torr to give 133.27 g of α,α',α'',α'''-tetrakis-[ω[(hydroxyethoxypropyldimethylsilyl) oxy]poly(dimethylsilyene)]]silane(9Cl) (IIb) as a colourless oil (n=1.75, MW 986).

Example E

This example illustrates the preparation of hydroxyethoxypropyl terminated 3.55%-(methylmethacryloxypropyl methyl siloxane)(dimethyl siloxane) copolymer (Ie).

25.22 g of 1,3,5,7-tetramethylcyclotetrasiloxane, and 400.00 g of α,ω-bis(hydroxyethoxypropyl) polydimethylsiloxane (MW 954) were mixed in a glass bottle containing a magnetic stirrer bar. 1.96 g of trifluoromethanesulfonic acid was added to the mixture and the bottle sealed with an air tight cap. The mixture was stirred vigorously for 3.5 hours at room temperature after which 20 g of sodium carbonate was added. The bottle was resealed and stirred for over night, after which the sodium carbonate was filtered off to give 417.78 g of hydroxyethoxypropyl terminated (methylhydrosiloxane) (dimethyl siloxane) copolymer intermediate.

In a three-neck 3 L round bottomed flask equipped with a water cooled condensed equipped with a silica gel drying tube, a 250-mL pressure compensating dropping funnel, and a thermometer were placed 417.78 g of hydroxyethoxypropyl terminated (methylhydrosiloxane)(dimethyl siloxane) copolymer intermediate given above and 300 mL of dry toluene. The mixture was heated, whilst stirring, to 60° C. 0.6 mL of a toluene solution of Karstedt's catalyst (containing 66.04× $10^{-6}$ moles Pt/mL) was added to the mixture. 70.48 g of allylmethacrylate was added drop wise to the mixture from the dropping funnel. The addition was made over a 20 minute period during which time the temperature of the mixture rose to 72° C. after which the reaction mixture was maintained at 70° C. for 18 hour. Silanic hydrogen content was checked by infrared spectroscopy. When no trace was detectable the reaction was considered to be complete. The reaction mixture was allowed to cool to room temperature and treated with 20 g of activated carbon for 18 hours whilst stirring. The reaction mixture was filtered through celite to remove the carbon followed by filtration through a 0.2 μm Teflon filter. 0.094 g of MEHQ was added to the toluene solution and then the toluene was removed by rotary evaporator at 60° C. under a reduced pressure of 20 torr. The mixture was transferred to a kugelrohr distillation apparatus and stripped of low molecular weight species at 50° C. under a reduced of $1 \times 10^{-1}$ torr for 20 minutes, this process was repeated 3 times to give 403.70 g of hydroxyethoxypropyl terminated 3.55%-(methylmethacryloxypropyl methyl siloxane)(dimethyl siloxane) copolymer (Ie) as a pale yellow oil (x=9.56, y=0.352, MW 1039).

The synthetic routes for Examples A to E are shown in Scheme 1 below.
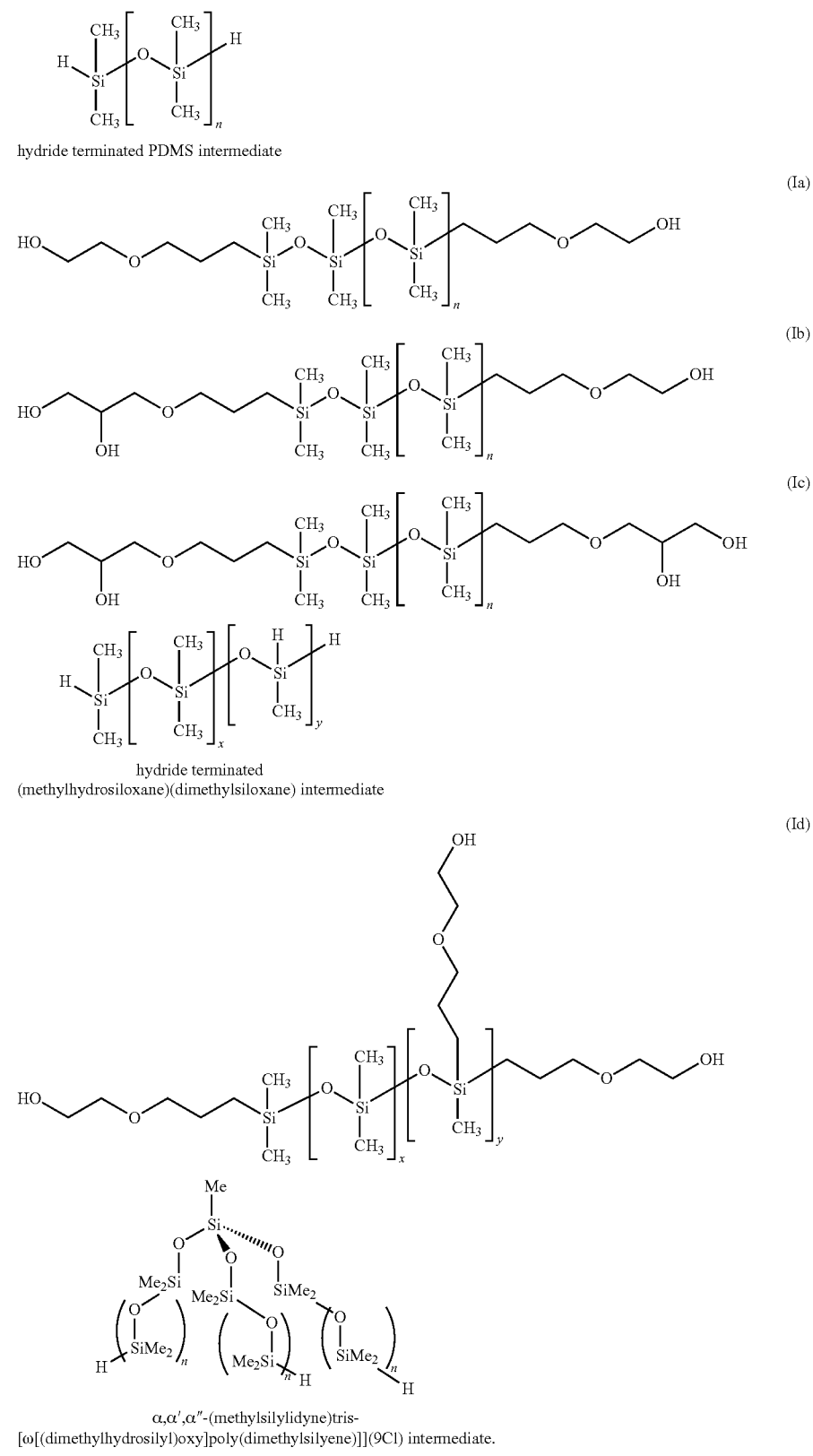

(IIa)
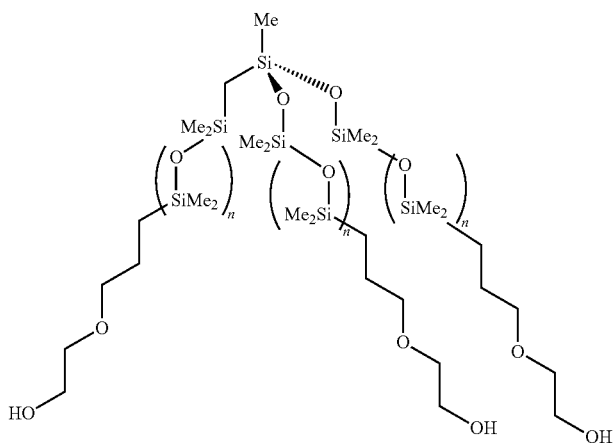
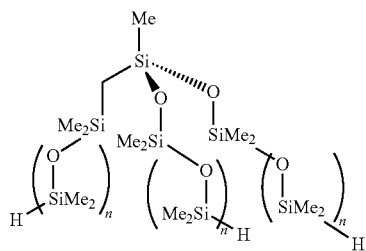
α,α′,α″-(methylsilylidyne)tris-
[ω[(dimethylhydrosilyl)oxy]poly(dimethylsilyene)]](9Cl) intermediate.
(IIb)
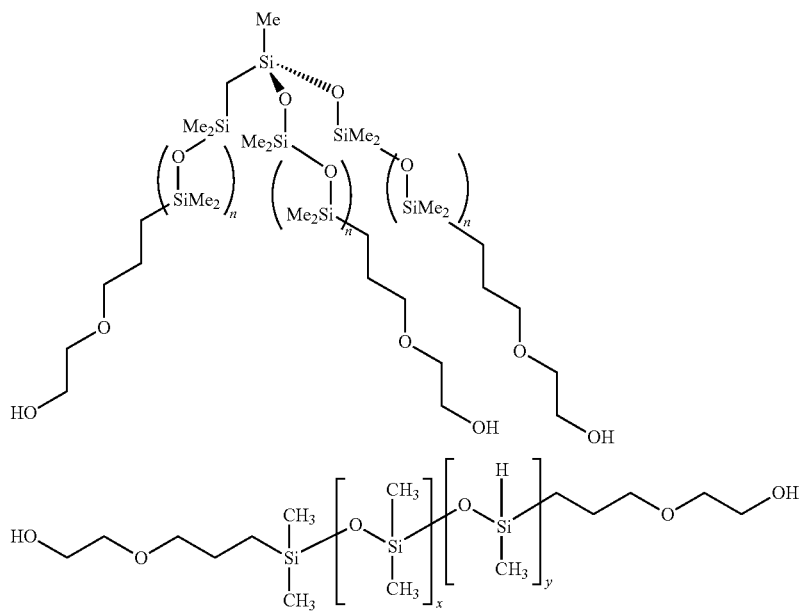
hydroxyethoxypropyl terminated
(methylhydrosiloxane)(dimethyl
siloxane) copolymer intermediate

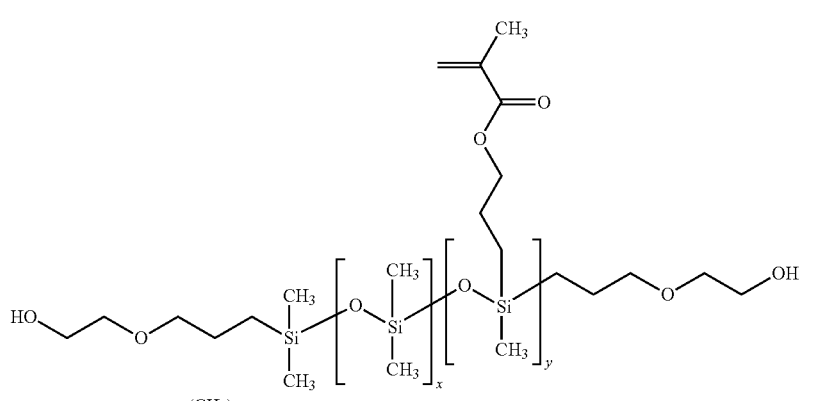

(Ie)

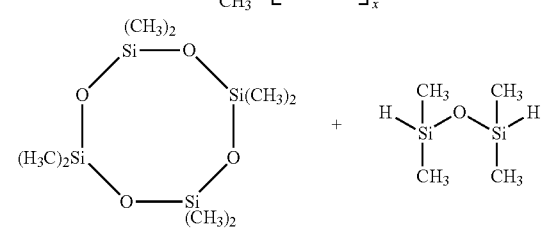

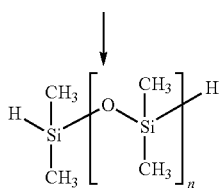

hydride terminated PDMS intermediate

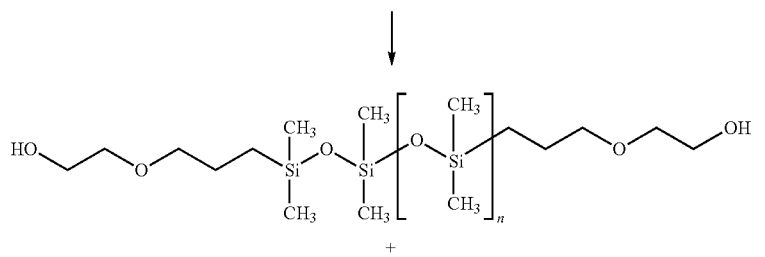

(Ia)

+

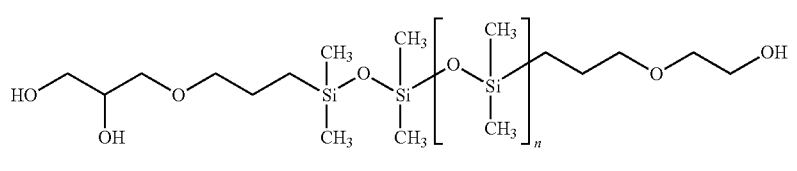

(Ib)

+

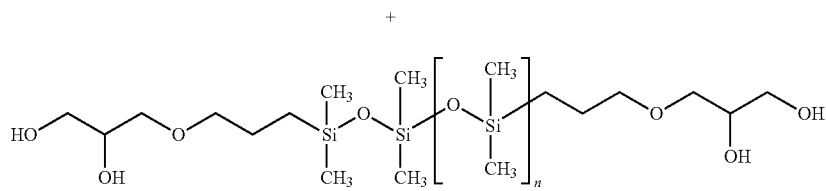

(Ic)

Gel Synthesis

The gels were synthesised using different processes:
One Shot Process—All reactants of the gel were added and mixed together.
Two Stage Process—The gel synthesis in this process occurred with the formation of a di-functional isocyanate terminated pre-polymer in the first stage followed by the addition of the hydroxyl terminated multifunctional polyols.
Slow Addition Process—All the reactants of the gel were mixed in together but the polyols are added to the diisocyanate in a drop wise fashion.
Sequenced Slow Addition—This is similar to the slow addition process except that certain polyol functionalities are added before the others.

UV Curing—For the process of curing with ultra-violet light, a formulation containing an unsaturation in the polyol segment was prepared. A photoinitiator was added to the mixture and this in the presence of an externally supplied, long wavelength, ultraviolet radiation resulted in the formation of a cross linked gel.

Example 1

One Shot Process 4,4'-Diphenylmethane diisocyanate (MDI) was accurately weighed in a paper cup. In a Schott bottle, a mixture of polyol adduct viz. polyethylene monoalcohol, polydimethylsiloxane (Mw 1000 & 2000), voranol-2070 and N,N,N'-tri(2-hydroxypropyl)-N'-hydroxyethylethylenediamine (Poly Q 40-800) was added to the MDI in bulk and stirred for 4 minutes and placed in the oven at 70° C. overnight to cure.

The formulations, with the parts by weight (PBW) of all the reactants, stoichiometry, average functionality and the results of the extractables are set out in Table 2 below.

TABLE 2

| NCO/OH | MDI | Diol | Triol | Tetra-ol | Ext (%) | $F_{ave}$ | $\eta^*$ 0.01 | $\eta^*$ 10 |
|---|---|---|---|---|---|---|---|---|
| 0.6 | 20.79 | PDMS-2000 10 | 87 | 3 | 14.2 | 2.77 | — | — |
| 0.7 | 24.25 | PDMS-2000 10 | 87 | 3 | 15.6 | 2.74 | — | — |
| 0.5 | 16.76 | PDMS-2000 15 | 82 | 3 | 31.2 | 2.8 | — | — |
| 0.6 | 20.11 | PDMS-2000 15 | 82 | 3 | 30.5 | 2.76 | — | — |
| 0.4 | 21.55 | PTMO 10 | 87 | 3 | 15.1 | 2.75 | 421.8 | 273 |
| 0.4 | 21.39 | PDMS-1000 12 | 85 | 3 | 7.82 | 2.74 | 407 | 122 |
| 0.4 | 22.23 | PTMO 20 | 85 | 3 | 21.17 | 2.71 | 565.2 | 113 |
| 0.4 | 20.57 | PDMS-1000 16 | 80 | 2.75 | 13.4 | 2.72 | 881.3 | 192 |
| 1 | 32.32 | PDMS-1000 90 | 10 | 2 | 4.66 | 2.19 | — | — |

Example 2

Two Stage Process

The gels were prepared in two steps; preparation of prepolymer with difunctional polyols to get desired NCO index (NCO/OH) followed by reaction of pre-polymer with multifunctional polyols to get desired stoichiometric imbalance "r".

The ratio of the reactants "r" can be compared to the stoichiometry NCO to OH group:

$$r = \Sigma f \cdot n_{Af} / \Sigma g \cdot n_{Bg}$$

in which f and $n_{Af}$ are the functionality and number mole of NCO, g and $n_{Bg}$ are the functionality and the total number mole of the OH group materials such as polydimethylsiloxane (Mw 2000), 1,4-butanediol, voranol-2070 and N,N,N'-tri(2-hydroxypropyl)-N'-hydroxyethylethylenediamine (Poly Q 40-800).

Preparation of Prepolymer

The PDMS (MW 2000) was degassed at 70° C. under vacuum prior to synthesis. Molten MDI was placed in a three necked round bottom flask which was fitted with a mechanical stirrer and nitrogen inlet. The flask was placed in an oil bath set at 70° C. The degassed PDMS was added to MDI and was stirred by mechanical stirrer under a nitrogen atmosphere for 2 hours.

After completion the addition of PDMS, the temperature of the oil bath was increased to 80° C. The prepolymer stirred at 100 rpm under nitrogen atmosphere for 2 h. The prepolymer was degassed for 1 hour under vacuum. Prepolymers with 2% and 4% free NCO contents were made. The free NCO % is based on the ratio of excess NCO functional group by the amount of prepolymer in weight percentage. The excess NCO functional group is determined by the amount of excess MDI which contains 33.6% by weight NCO group. The excess MDI is the amount which remains after reaction with hydroxyl terminated PDMS.

Reaction with Multifunctional Polyol

A mixture of polyol adducts viz. 1,4-butanediol (BDO)/bis-hydroxy butyl tetramethyldisiloxane (BHTD), voranol-2070 and N,N,N'-tri(2-hydroxypropyl)-N'-hydroxyethylethylenediamine (Poly Q 40-800) stirring at 70° C. The adduct was then added to the prepolymer and allowed to mix using a high shear mechanical stirrer for 4 minutes at 5000 rpm. The polymer was transferred into the oven and allowed to cure in a nitrogen blanketed oven overnight at 70° C.

The parts by weight (PBW) of the reactants in the formulations, stiochiometries, average functionality and extractables (%) are given in Table 3, 4 and 5 below. The amount of multifunctional polyols is based on 100 g of prepolymer.

TABLE 3

| Pre-polymer NCO/OH | MDI | Diol | | Triol Voranol | Tetra-ol Poly-Q | r | $F_{ave}$ | $\eta^*$ 0.01 | $\eta^*$ 10 |
|---|---|---|---|---|---|---|---|---|---|
| 2.9 | 37.80 | | | 50.43 | 0 | 0.5 | 2.64 | — | — |
| 2.9 | 37.80 | | | 35.42 | 0 | 0.75 | 2.52 | — | — |
| 2.9 | 37.80 | | | 29.5 | 0 | 0.9 | 2.45 | — | — |
| | 37.80 | BDO | BHTD | | | | | | |
| 2.9 | 37.80 | 10 | | 111.5 | 0 | 0.35 | 2.47 | — | — |
| 2.9 | 37.80 | | 10 | 111.5 | 0 | 0.35 | 2.56 | — | — |
| 2.9 | 37.80 | | | 112 | 5 | 0.35 | 2.67 | — | — |
| 2.9 | 37.80 | | | 95 | 10 | 0.35 | 2.75 | — | — |
| 2.9 | 37.80 | | | 115 | 4 | 0.35 | 2.71 | — | — |
| 2.9 | 37.80 | | 5 | 117 | 10 | 0.35 | 2.62 | — | — |

TABLE 4

| Pre-polymer NCO/OH | MDI | Triol Voranol | Tetra-ol Poly-Q | r | Extractables (%) | $F_{ave}$ | $\eta^*$ 0.01 | $\eta^*$ 0.01 |
|---|---|---|---|---|---|---|---|---|
| 2.2 | 28.23 | 49.5  | 0    | 0.6   | 27.1  | 2.45 | — | — |
| 2.2 | 28.23 | 67.3  | 1.5  | 0.45  | 12.24 | 2.58 | — | — |
| 2.2 | 28.23 | 58.1  | 1.5  | 0.5   | 13.94 | 2.55 | — | — |
| 2.2 | 28.23 | 52.42 | 1    | 0.55  | 21.54 | 2.52 | — | — |
| 2.2 | 28.23 | 50.75 | 1.5  | 0.55  | 28.01 | 2.52 | — | — |
| 2.2 | 28.23 | 50.82 | 0.5  | 0.575 | 19.28 | 2.48 | — | — |
| 2.2 | 28.23 | 49.17 | 1    | 0.575 | 14.86 | 2.49 | — | — |
| 2.2 | 28.23 | 54.11 | 0.75 | 0.55  | 16.15 | 2.5  | — | — |

TABLE 5

| Pre-polymer NCO/OH | MDI | Triol Voranol | Tetra-ol Poly-Q | r | Extractables (%) | $F_{ave.}$ | $\eta^*$ 0.01 | $\eta^*$ 0.01 |
|---|---|---|---|---|---|---|---|---|
| 2.2 | 28.23 | 66.7  | 1.5  | 0.45  | 21.96 | 2.58 | — | — |
| 2.2 | 28.23 | 60    | 0.75 | 0.5   | 29.09 | 2.53 | — | — |
| 2.2 | 28.23 | 52.7  | 0.75 | 0.55  | 19.5  | 2.5  | — | — |
| 2.2 | 28.23 | 51.87 | 1    | 0.55  | 16.17 | 2.51 | — | — |
| 2.2 | 28.23 | 50.2  | 1.5  | 0.55  | 23.74 | 2.52 | — | — |
| 2.2 | 28.23 | 47.3  | 0.5  | 0.6   | 13.83 | 2.46 | — | — |
| 2.2 | 28.23 | 42.97 | 1    | 0.625 | 15.16 | 2.46 | — | — |
| 2.2 | 28.23 | 49.93 | 0.75 | 0.575 | 17.71 | 2.49 | — | — |
| 2.2 | 28.23 | 47.73 | 1.5  | 0.575 | 18.8  | 2.51 | — | — |
| 2.2 | 28.23 | 46.9  | 0.75 | 0.6   | 9.82  | 2.47 | — | — |
| 2.2 | 28.23 | 64.1  | 1    | 0.6   | 12.33 | 2.48 | — | — |
| 2.2 | 28.23 | 44.48 | 1.5  | 0.6   | 20.1  | 2.49 | — | — |

Example 3

Slow Addition Process 4,4'-Diphenylmethane diisocyanate (MDI) was accurately weighed in a Schott bottle equipped with a magnetic stirrer and placed in an oil bath at 80° C. In another Schott bottle, a mixture of polyol adduct viz. polydimethylsiloxane (Mw 1000-1300), hydroxyethoxypropyl terminated 9.09%-(hydroxyethoxypropyl methyl siloxane) (dimethyl siloxane) copolymer (Mw 1210)/α,α',α"-(methylsilylidyne)tris-[ω [(hydroxyethoxypropyldimethylsilyl) oxy]poly (dimethylsilyene)]] (Mw 1000-5000) and α,ω-bis(6,7-dihydroxyethoxypropyl) polydimethylsiloxane (Mw 400-500)/α,α',α",α'"-tetrakis-[ω[(hydroxyethoxypropyldimethylsilyl) oxy]poly (dimethylsilyene)]]silane (Mw 1400-1600) placed in an oil bath at 80° C. The adduct was added to MDI at the rate of 1 ml/min with constant stirring under a nitrogen atmosphere till the viscosity built up. With an increase in viscosity, the addition of adduct was increased to 2 ml/min until the viscosity increased again. The highly viscous solution was then transferred to a paper cup and placed in the oven at 70° C. overnight to cure.

The parts by weight (PBW) of the reactants in the formulations, stoichiometries, average functionalities and extractables (%) are given in Table 6 below:

TABLE 6

| NCO/OH | MDI | Diol PDMS-1000 | Triol Voranol | Tetra-ol PolyQ | Extraction (%) | $F_{ave}$ | $\eta^*$ 0.01 | $\eta^*$ 0.01 |
|---|---|---|---|---|---|---|---|---|
| 0.75 | 21.66 | 90 | 10  | 0    | 29.34 | 2.1  | 3596 | 331 |
| 0.8  | 32.11 | 90 | 10  | 0    | 17.79 | 2.1  | —    | —   |
| 0.7  | 20.27 | 95 | 6   | 0.5  | 30    | 2.10 | 2052 | 182 |
| 0.7  | 20.52 | 95 | 7.5 | 0.25 | 30.96 | 2.10 | 1304 | 292 |
| | | | Si Triol MW1151 | Si-tet- MW430 | | | | |
| 0.7 | 19.62 | 75   | 25   | 0.2 | 19.58 | 2.18 | 1705 | 113 |
| 0.7 | 19.73 | 72.5 | 27.5 | 0.2 | 22.46 | 2.19 | —    | —   |
| | | PDMS-1000 | Si Triol MW1151 | | | | | |
| 0.7 | 19.78 | 75 | 25 | 0.4 | 18.56 | 2.18 | —    | —   |
| 0.7 | 20.53 | 80 | 25 | 0.2 | 18.27 | 2.17 | 1189 | 136 |
| 0.7 | 19.39 | 80 | 20 | 0.2 |       | 2.15 | —    | —   |

TABLE 6-continued

| NCO/OH | MDI | Diol PDMS-1000 | Triol Voranol | Tetra-ol PolyQ | Extraction (%) | $F_{ave}$ | $\eta^*$ 0.01 | $\eta^*$ 0.01 |
|---|---|---|---|---|---|---|---|---|
| | | | | Si-tet-MW1140 | | | | |
| 0.7 | 19.51 | 75 | 25 | 0.2 | 22.22 | 2.17 | 2900 | 243 |
| | | | | Si-tet-MW1519 | | | | |
| 0.7 | 19.50 | 75 | 25 | 0.2 | 16.8 | 2.17 | 839 | 261 |
| 0.7 | 20.42 | 80 | 25 | 0.2 | 20.75 | 2.16 | 716 | 173 |
| | | | | Si-tet-MW1140 | | | | |
| 0.7 | 20.43 | 80 | 25 | 0.2 | 21.14 | 2.16 | 2067 | 213 |
| | | Si-Triol MW1210 T shape | | Si-tet-MW1519 | | | | |
| 0.7 | 20.14 | 80 | 25 | 0.2 | 25.97 | 2.16 | 3244 | 159 |
| | | | | Si-tet-MW430 | | | | |
| 0.7 | 20.26 | 80 | 25 | 0.2 | 28.57 | 2.16 | 1835 | 212 |
| 0.7 | 19.17 | 80 | 20 | 0.2 | 23.96 | 2.14 | 1313 | 228 |
| | | | | Si-tet MW1519 | | | | |
| 0.7 | 19.06 | 80 | 20 | 0.2 | 12.18 | 2.13 | 605.6 | 196 |
| | | | | Si-tet-MW430 | | | | |
| 0.7 | 19.71 | 80 | 22.5 | 0.2 | 24.46 | 2.15 | 356.2 | 290 |
| | | | | Si-tet-MW1519 | | | | |
| 0.7 | 19.60 | 80 | 22.5 | 0.2 | 19.78 | 2.14 | 878.7 | 120 |
| | | | | Si-tet-MW430 | | | | |
| 0.7 | 18.63 | 80 | 17.5 | 0.2 | | 2.13 | 1435 | 160 |

Example 4

Sequenced Slow Addition Process 4,4'-Diphenylmethane diisocyanate (MDI) was accurately weighed in a Schott bottle equipped with a magnetic stirrer and placed in an oil bath at 70° C. In another Schott bottle, a mixture of polyols viz. polydimethylsiloxane (Mw 1000/2000) and voranol-2070 placed in an oil bath at 70° C. The mixture of polyols was added to MDI with constant stirring by magnetic stirrer in 5 minutes intervals (1 ml/5 min). N,N,N'-tri(2-hydroxypropyl)-N'-hydroxyethylethylenediamine (Poly Q 40-800) was added finally and continued stirring until the viscosity increases. The highly viscous solution was then transferred to a paper cup and placed in the oven at 70° C. overnight to cure. The results are shown in Table 7 below.

TABLE 7

| NCO/OH | MDI | PDMS | Triol | Tetra-ol | Ext (%) | $F_{ave.}$ | $\eta^*$ 0.01 | $\eta^*$ 0.01 |
|---|---|---|---|---|---|---|---|---|
| 0.3 | 5.76 | 24.7 | 75 | 0.3 | 30.9 | 2.72 | — | — |
| 0.3 | 12.93 | 24.9 | 75 | 0.1 | 24.1 | 2.71 | — | — |
| 0.7 | 22.05 | 80 | 20 | 0 | 21.24 | 2.2 | 2438 | 124 |

4,4'-Diphenylmethane diisocyanate (MDI) was accurately weighed in a Schott bottle equipped with a magnetic stirrer and placed in an oil bath at 70° C. The addition of polyols mixture was added in the following manner: i) polydimethylsiloxane (Mw 1000) was added first; ii) a mixture of polyethylene monoalcohol and voranol-2070 was added last. The polyols were added to MDI while stirring by magnetic stirrer in five minute interval (1 ml/5 min). The resulting reaction mixture was allowed to stir until the viscosity increases. The highly viscous solution was then transferred to a paper cup and placed in the oven at 70° C. overnight to cure. The results are shown in Table 8 below:

TABLE 8

| NCO/OH | MDI | PDMS 1000 | Triol | Monool | $F_{ave.}$ |
|---|---|---|---|---|---|
| 1.7 | 15.41 | 34.59 | 11.95 | 11.95 | 2.16 |

4,4'-Diphenylmethane diisocyanate (MDI) was accurately weighed in a Schott bottle equipped with a magnetic stirrer and placed in an oil bath at 70° C. The addition of polyols mixture was added in the following manner: i) polydimethylsiloxane (Mw 1000) was added first; ii) voranol-2070 was added and iii) polyethylene monoalcohol was added finally. The polyols were added to MDI while stirring by magnet stirrer in 5 minute interval (1 ml/5 min). The resulting reaction mixture was allowed to stir until the viscosity increases. The highly viscous solution was then transferred to a paper cup and placed in the oven at 70° C. overnight to cure. The results are shown in Table 9 below:

TABLE 9

| NCO/OH | MDI | PDMS 1000 | Triol | Monool | $F_{ave.}$ | $\eta^*$ 0.01 | $\eta^*$ 0.01 |
|---|---|---|---|---|---|---|---|
| 1.7 | 15.41 | 34.59 | 11.95 | 11.95 | 2.16 | — | — |

4,4'-Diphenylmethane diisocyanate (MDI) was accurately weighed in a Schott bottle equipped with a magnet stirrer and placed in an oil bath at 70° C. The addition of polyols mixture was added in the following manner: i) 50% wt of polydimethylsiloxane (Mw 1000) was added first; ii) a mixture of 50% wt of polydimethylsiloxane (Mw 1000), and 50% wt of voranol-2070 was added second iii) a mixture of 50% wt of voranol-2070 and 100% wt of polyethylene monoalcohol was added finally. The polyols were added to MDI while stirring by magnet stirrer in 5 minute intervals (1 ml/5 min). The resulting reaction mixture was allowed to stir until the viscosity increases. The highly viscous solution was then transferred to a paper cup and placed in the oven at 70° C. overnight to cure. The results are shown in Table 10 below.

TABLE 10

| NCO/OH | MDI | PDMS 1000 | Triol | Monool | $F_{ave.}$ | $\eta^*$ 0.01 | $\eta^*$ 0.01 |
|---|---|---|---|---|---|---|---|
| 1.3 | 12.70 | 37.30 | 8.00 | 4.00 | 2.14 | — | — |

Example 5

UV Curing

UV-curing systems rely upon externally-supplied, long wavelength, ultraviolet radiation to produce free radicals within the material. UV light does not usually have sufficient energy levels to interact with the reactive groups of the molecules and generate free radicals. When a photoinitiator is added to the formulation, which when exposed to UV of a specific wavelength, absorbs the UV light and produces free radicals which start the cross linking process and results in virtually instant polymerisation. In the free radical formulation the reaction will only continue as long as the formulation is subjected to the UV light.

The appropriate amount of synthesised hydroxyethoxypropyl terminated 3.55%-(methylmethacryloxypropyl methyl siloxane) (dimethyl siloxane) copolymer of Mw 1039 was accurately weighed in a Petri dish and mixed thoroughly using a spatula with required weight percentage (w/w) of photoinitiator (Irgacure 819) (varying percentage from 0.25%-2% w/w) in ~1 ml of toluene and placed in the UV chamber (UV lamp 5 mW, 366 nm) for 48 h to cure.

In another example using UV curing, the molten MDI was placed in a three necked round bottom flask which was fitted with a mechanical stirrer and nitrogen inlet. The flask was placed in an oil bath set at 60° C. The synthesised hydroxyethoxypropyl terminated 3.55%-(methylmethacryloxypropyl methyl siloxane) (dimethyl siloxane) copolymer of Mw 1039 was added to MDI and stirred by mechanical stirrer under a nitrogen atmosphere for 2 h and was degassed for 1 h under vacuum. The chain extended polymer accurately weighed in a petri dish and mixed thoroughly using a spatula with required weight percentage (w/w) of photoinitiator (Irgacure 819) (varying percentage from 0.25%-2% w/w) in ~1 ml of toluene and placed in the UV chamber (home built) (UV lamp 5 mW, 366 nm) for 48 h to cure. The results are shown in Table 11 below.

TABLE 11

| NCO/OH | MDI (Moles) | Vinyl double bonded diol (Moles) | $F_{ave.}$ | $\eta^*$ 0.01 | $\eta^*$ 0.01 |
|---|---|---|---|---|---|
| 1.73 | 0.1144 | 0.066 | 2.89 | — | — |

In another example using UV curing, the molten MDI was placed in a three necked round bottom flask which was fitted with a mechanical stirrer and nitrogen inlet. The flask was placed in an oil bath set at 60° C. The synthesised hydroxyethoxypropyl terminated 3.55%-(methylmethacryloxypropyl methyl siloxane) (dimethyl siloxane) copolymer of Mw 1039 was added to MDI and stirred by mechanical stirrer under a nitrogen atmosphere for 2 h and was degassed for 1 h under vacuum. PDMS 1000/2000 was then added to prepolymer and allowed to mix using a shear mechanical stirrer for 4 min at 5000 rpm. The polymer then accurately weighed for different formulation in a petri dish and mixed with required weight percentage (w/w) of photoinitiator (Irgacure 819) (varying percentage from 0.25%-2% w/w) in ~1 ml of toluene thoroughly using a spatula and placed in the UV chamber (home built) (UV lamp 5 mW, 366 nm) for 48 h to cure. Results are shown in Table 12 below.

TABLE 12

| NCO/OH | MDI (Moles) | Vinyl double bonded diol (Moles) | PDMS 1000 (Moles) | $F_{ave.}$ | $\eta^*$ 0.01 | $\eta^*$ 0.01 |
|---|---|---|---|---|---|---|
| 0.67 | 0.132 | 0.066 | 0.132 | 2.273 | — | — |

Example 6

Cytotoxicity Study Using the Iso-Elution Method

Purpose

To evaluate the biocompatibility of a test article extract using an in vitro mammalian cell culture test. This study is based on the requirements of the International Organization for Standardization 10993; Biological Evaluation of Medical Devices, Part 5: Tests for Cytotoxicity: in vitro Methods.

Ratio of Test Material to Extraction Vehicle:

Material thickness less than 0.5 mm—ratio of 60 $cm^2$:10 ml (based on the USP ratio 120 $cm^2$:20 ml)

Extraction Vehicles:

Single strength Minimum Essential Medium supplemented with 5% serum and 2% antibiotics (1×MEM)

Extraction Conditions:

The extraction conditions shall attempt to exaggerate the clinical use conditions so as to define the potential toxicological hazard; however, they should not in any instance cause physical changes such as fusion or melting, which results in a decrease in the available surface area. A slight adherence of the pieces can be tolerated.

Control Articles:

Negative Control: high density polyethylene, will be prepared based on a ratio of 60 $cm^2$:20 ml extraction vehicle. A single preparation of the material will be made, and will be extracted using the same conditions as described for the test article.

Reagent Control: A single aliquot of the extraction vehicle without test material will be prepared using the same conditions as described for the test article.

Positive Control: Current positive control material*, tin stabilized at polyvinylchloride, will be prepared based on a ratio of 60 $cm^2$:20 ml extraction vehicle. A single preparation of the material will be made and extracted at 37° C. for. 24 hours. Serial dilutions will be prepared for an end-point titration procedure.

*NOTE: The current positive control material has been qualified as an acceptable replacement for the USP recommended control material.

Test System and Justification:

Mammalian cell culture monolayer, L-929, mouse fibroblast cells, (ATCC CCL 1, NCTC Clone 929, of strain L, or equivalent source), will be used. In vitro mammalian cell culture studies have been used historically to evaluate cytotoxicity of biomaterials and medical devices (Wilsnack, et al., 1973).

Test System Management:

L-929, mouse fibroblast cells, (ATCC CCL 1, NCTC Clone 929, of strain L, or equivalent source) will be propagated and maintained in open wells containing single strength Minimum Essential Medium supplemented with 5% serum and 2% antibiotics (1×MEM) in a gaseous environment of 5% carbon dioxide ($CO_2$). For this study, 10 $cm^2$ wells will be seeded, labeled with passage number and date, and incubated at 37° C. in 5% CO to obtain confluent monolayers of cells prior to use. Aseptic procedures will be used in the handling of the cell cultures following approved Standard Operating Procedures.

Methods and Route of Administration:

Each culture well will be selected which contains a confluent cell monolayer. The growth medium in triplicate cultures will be replaced with 2 ml of the test extract. Similarly, triplicate cultures will be replaced with 2 ml of the reagent control, negative control extract and the undiluted and each titer of the positive control. Each well will be incubated at 37° C. in 5% $CO_2$ for 48 hours.

Following incubation, the cultures will be examined microscopically (100×) to evaluate cellular characteristics and percent lysis.

Evaluation Criteria and Statistics:

The confluency of the monolayer will be recorded as (+) if present and (−) if absent. In addition, the color of the test medium will be observed and compared to the negative control medium. Each culture well will be evaluated for percent lysis and cellular characteristics using the following criteria:

| Grade | Reactivity | Observations | |
|---|---|---|---|
| 0 | None | Discrete intracytoplasmic granules | No lysis |
| 1 | Slight | Not more than 20% of the cells are round, loosely attached, and without intracytoplasmic granules | Not more than 20% lysis |
| 2 | Mild | Not more than 50% of the cells are round and devoid of intracytoplasmic granules | Not more than 50% lysis. |
| 3 | Moderate | Not more than 70% of the cell monolayer contains rounded cells | Not more than 70% lysis |
| 4 | Severe | Nearly complete destruction of the cell monolayer | Greater than 70% lysis |

For the test to be valid, the reagent control and the negative control must have a reactivity of none (grade 0) and the positive control must be a grade 3 or 4. The test sample meets the requirements of the test if the biological response is less than or equal to grade 2 (mild). The test will be repeated if the controls do not perform as anticipated and/or if all three test wells do not yield the same conclusion.

References for Example 6:

21 CFR 58 (GLP Regulations).

International Organization for Standardization 10993: Biological Evaluation of Medical Devices, Part 5: Tests for Cytotoxicity: in vitro Methods.

United States Pharmacopeia (USP), current edition.

Wilsnack, R. E., "Quantitative Cell Culture Biocompatibility Testing of Medical Devices and Correlation to Animal Tests" Rio materials, Medical Devices and Art/Icfal Organs 4 (1976): 235-261.

Wilsnack R. B., P. S. Meyer and 3.0. Smith, 'Human Cell Culture Toxicity Testing of Medical Devices and Correlation to Animal Tests,' Biomaterials, Medical Devices and Artificial Organs 1 (1973): 543-562.

Example 7

Sensitization Study in the Guinea Pig (Maximization Method)

Purpose of the Study:

The objective of the maximization test in the guinea pig is to identify the potential for dermal sensitization. The Magnusson and Kligman method has been effective in identifying a variety of allergies. This study will be based on the requirements of the International Organization for Standardization 10993: biological Evaluation of Medical Devices, Part 10: Tests for Irritation and Sensitization.

Test Article:

The sample will be prepared as follows:

1. Ratio of Test Article Extraction Vehicle:

Material thickness less than 0.5 mm—ratio of 120 $cm^2$ 20 ml

2. Extraction Vehicle:

0.9% sodium chloride USP solution (SC)

cottonseed oil, NF (CSO)

3. Extraction Condition:
   37° C., 72 hours (2 hours)

Control Article:

The vehicle used to prepare the extract will be prepared in the same manner as the extract (but without test article) serve as the control measure. Untreated skin will serve as an additional control reference for scoring dermal reactions during the challenge phase.

Test System:

| | |
|---|---|
| Species: | Guinea pig (*Cavia porcellus*) |
| Strain: | Crl: (HA) BR |
| Source: | Charles River Laboratories |
| Sex: | No particular gender is prescribed for this test. If females are used) they will be nulliparous and not pregnant. |
| Body Weight Range: | 300-500 grams at identification |
| Age: | Young adults |
| Acclimation Period: | Minimum 5 days |
| Number of Animals: | 15 (per extract) |
| Identification Method: | Ear punch |

Justification of Test System:

The Hartley albino guinea pig has been used historically for sensitization studies (Magnusson and Kilgman, 1970). The guinea pig is believed to be the most sensitive animal model for this type of study. The susceptibility of the Hartley strain to a known sensitizing agent, 1-chloro-2,4-dinitrobenzene (DNCB) has been substantiated with this method.

Test and Control Article Preparation:

Fresh extracts will be prepared at each phase of the study as previously indicated (see Test Article). If the test material is suitable for patching, a topical application of the test sample (2 cm×2 cm patch) will be used at the challenge. The vehicle used to prepare the extract will be prepared in the same manner as the extract (but without test article) to serve as the control measure.

Methods and Route of Administration:

The day prior to treatment, 15 guinea pigs per extract (10 test, 5 control) will be weighed and identified. The fur from the dorsoscapular area of the animals will be removed with an electric clipper.

Induction I:

Three pair of intradermal injections will be administered to the animals within an approximate 2 cm×4 cm area the dorsoscapular region as follows:

Control Animals:
a. 0.1 ml of 50:50 (v/v) mixture of Freund's Complete Adjuvant (FCA) and the chosen vehicle
b. 0.1 ml of vehicle
c. 0.1 ml of a 1:1 mixture of the 50:50 (v/v) FCA and the vehicle Test Animals:
a. 0.1 ml of 50:50 (v/v) mixture of FCA and the chosen vehicle
b. 0.1 ml of test extract
c. 0.1 ml of a 1:1 mixture of the 50:50 (v/v) FCA and the test extract To minimize tissue sloughing the 'a" and "c' injections will be slightly deeper than "b'. Site 'c" will be injected slightly more caudal than site 'b".

Induction II:

Six days later, the injection sites will be clipped free of fur again and treated with 0.5 to 1 g of a 10% (w/w) sodium lauryl sulfate (SLS) suspension prepared by mixing the powdered SLS with petrolatum. The day following the SLS treatment, any remaining SLS residue will be gently wiped from the area with gauze.

A 2 cm×4 cm filter paper patch (3MM, Whatman), saturated with 0.3 ml of the extract preparation or vehicle, will be applied over the same injection area and secured with a non-reactive tape. The trunk of each animal will then be wrapped snugly with an elastic band for 48 hours (±2 hours).

Challenge:

At 13 days after unwrapping induction II wraps, the fur will be clipped from the sides and flanks of all guinea pigs. On the following day, a nonwoven cotton disk backed by a flexible chamber (e.g. Hill Top Chamber®) and semiocclusive hypoallergenic tape, will be saturated with 0.3 ml of freshly prepared test material extract and applied to the right flank or dorsum of each animal. In addition, the vehicle control will be patched to the left flank or dorsum of each animal. An approximate 2 cm×2 cm section of test material itself (if appropriate) will be applied to the right flank.

The trunk of each animal will be wrapped for 24 hours (±2 hours). At patch removal the sites will be wiped with gauze. At 24 hours (±2 hours) after patch removal, the challenged sites and surrounding area will be shaved. The sites will be examined for signs of ahy irritation or sensitization reaction, as indicated by erythema and edema at a minimum of 2 hours and a maximum of 4 hours following the shave and at 48 (±2 hours) and 72 (±2 hours) hours after removal of the dressings. Prior to scoring, each site will be wiped gently with a 35% isopropyl alcohol gauze sponge.

Should the original challenge results prove to be equivocal, the animals may be rechallenged with a fresh test extract and vehicle control approximately 7 days after the first challenge patch application. The rechallenge will be conducted in the same manner as the challenge but at virgin sites on the opposite flank. After the test is completed, all animals will be handled in accordance with approved procedures.

Evaluations and Statistics:

Daily challenge scores for reactions will be recorded at 24, 48 and 72 hours after patch removal in accordance with the following Table:

| ERYTHEMA (ER) | | EDEMA (ED) | |
|---|---|---|---|
| Reaction | Numerical Grading | Reaction | Numerical Grading |
| No erythema | 0 | No edema | 0 |
| Slight erythema | 1 | Slight edema | 1 |
| Well-definded erythema | 2 | Well-defined edema | 2 |
| Moderate erythema | 3 | Moderate edema | 3 |
| Severe erythema to slight eschar formulation | 4 | Severe edema | 4 |

Any other observation relating to the site will be footnoted.

The responses will be compared within the test animal group and between test and control conditions. Control conditions are (1) the vehicle control solution on the test animals and (2) the test extract, control solution and biomaterial (if applied) on the control animals.

In the final analysis of data, consideration will be given to the overall pattern, intensity, duration, and character of reactions of the test as compared to the control conditions. Statistical manipulation of data is not applicable to this study. An effect interpreted as "irritation" is generally observed at 24 hours, but diminishes thereafter, and is also concurrently present as a transient response in the control animals. Closed patches typically show maximal sensitization readings 48 to 72 hours after patch removal in the test condition but not in the control condition. Grades of 1 or greater in the test group generally indicate sensitization, provided that grades of less than 1 are observed on the control animals. If grades of 1 or greater are noted on control animal then the reactions of test animals which exceed the most severe control reaction are considered to be due to sensitization.

Background or artifactual reactions (e.g., from fur clipping, patch chamber edge, nonspecific FCA effects) will not be considered as evidence of a sensitization response. The treatment with FCA and occlusive dressings may lower the threshold level for skin irritation.

If the test group has a greater number of animals showing responses that are not greater than the control animals, a rechallenge may be conducted. The rechallenge will be conducted approximately 7 days after the first challenge at virgin sites on the opposite flank of the animals. Absence of dermal response at rechallenge may nullify earlier findings. Recurring observations in at least one of the same animals verify earlier findings.

References for Example 7:

21 CFR 58 (GLP Regulations).

*Guide for the Care and Use of Laboratory Animals*, Institute for Laboratory Animal Research, National Academy of Sciences (Washington: National Academy Press, 1996).

International Organization for Standardization 10993: Biological Evaluation of Medical Devices, Part 10: Tests for Irritation and Sensitization.

Magnusson, B. and A. Kligman, Allergic Contact Dermatitis in the Guinea Pig (Springfield: C. H. Thomas, 192Q)

OLAW, Public Health Service Policy on Humane Care and Use of Laboratory Animals (NIH Publication)

United States Code of Federal Regulation (CFR) 9: The Animal Welfare Act.

Example 8

Acute Intracutaneous Reactivity Study in the Rabbit

Purpose:

The objective of this study is to evaluate the local dermal irritant effects of leachables extracted from the test article following intracutaneous injection in rabbits. This study will be based on the requirements of the International Organization for Standardisation 10993: Biological Evaluation of Medical Devices, Part 30: Tests for Irritation and Sensitization.

This study will be conducted in accordance with the Detailed information of the FDA Good Laboratory Practice (GLP) Regulations, 21CFR 58.

Test Article:

The sample will be prepared as follows:

1. Ratio of Test Article to Extraction Vehicle:
   Material thickness less than 0.5 mm—ratio of 120 cm$^2$; 20 ml.
3. Extraction Vehicle: 0.9% sodium chloride USP solution (SC).
4. Extraction Conditions: 37° C., 72 hours (±2 hours)

Control Article:

Reagent controls (extraction vehicle without test material) will be prepared in the same way and at the same time as the test extracts.

Test System:

| Species: | Rabbit (*Oryctolagus cuniculus*) |
|---|---|
| Strain: | New Zealand White |
| Source: | Single USDA licensed supplier |
| Sex: | No particular gender is prescribed in this test |
| Body Weight Range: | 2.0 kg or greater at selection |
| Age: | Young adults |
| Acclimation Period: | Minimum 5 days |
| Number of Animals: | Three per pair of extracts |
| Identification Method: | Ear tag |

Justification of Test System:

The intracutaneous injection test in rabbits is specified in the current ISO testing standards and has been used historically to evaluate biomaterial extracts.

Methods and Route of Administration:

The day prior to treatment, each rabbit will be weighed and clipped free of fur from the back and both sides of the spinal column to yield a sufficient injection area. The clipped area of the back will be wiped with a 70% alcohol soaked gauze pad just before injection and allowed to dry. Due to concern with the crowding and subsequent obscuring of injection sites, the test and control sites will not be cranial and caudal on the same side of the back as defined in the ISO standards. Each test extract will be administered in five intracutaneous injections of 0.2 ml each on the right side of each rabbit's back. Five reagent control injections will be injected similarly on the left side of the back. No more than two test extracts and the corresponding reagent controls will be injected into each animal. Injections will be about 2 cm apart. The appearance of the injection sites will be noted immediately after injection.

Observations for erythema and edema will be noted for each injection site at 24 (±2 hours), 48 (±2 hours) and 72 (±2 hours) hours after injection. Reactions will be scored on a 0 to 4 basis. Other adverse changes at the injection sites will also be noted. After the test is completed, all animals will be handled in accordance with approved procedures. The reactions will be evaluated according to the subjective rating scale as shown below:

| ERYTHEMA (ER) | | EDEMA (ED) | |
|---|---|---|---|
| 0 | No erythema | 0 | No edema |
| 1 | Very-slight erythema (barely perceptible) | 1 | Very-slight edema (barely perceptible) |
| 2 | Well-defined erythema | 2 | Well-defined edema (edges of area well-defined by definite raising) |
| 3 | Moderate erythema | 3 | Moderate edema (raised approximately 1 mm) |
| 4 | Severe erythema (beet redness) to eschar formation preventing grading of erythema) | 4 | Severe edema (raised approximately 1 mm, and extending beyond exposure area) |

Evaluations and Statistics:

No statistical analysis of the data will be performed. For each animal, the erythema and edema scores obtained at each time interval will be added together and divided by the total number of observations. This calculation will be conducted separately for each test extract and reagent control. The score for the reagent control will be subtracted from the score for the test extract to obtain the Primary Irritation Score. The Primary Irritation Score of each animal will be added together and divided by the total number of animals. The value obtained is the Primary Irritation Index (PII). The Primary Irritation Index is characterized by number and description as follows: 0-0.4 (negligible), 0.5-1.9 (slight), 2.0-4.9 (moderate), 5.0-8.0 (severe). If the response in the initial test is equivocal, additional testing may be necessary. Any adverse reaction noted in the test extract will be compared to the corresponding reagent control.

Report:

The final report will include a description of the methods employed, individual dermal scores for each test and control injection site, and the assessment of the results (Primary Irritation Scores and the Primary Irritation Index).

Records:

Test article and reagent control preparation data, dates of relevant activities (such as the study initiation and completion), the appearance of each injection site immediately after injection, individual dermal scores at 24, 48 and 72 hours, the Primary Irritation Score, and the Primary Irritation Index will be recorded.

References for Example 8:

21 CFR 58 (GLP Regulations).

*Guide for the Care and Use of Laboratory Animals*, Institute for Laboratory Animal Research, National Academy or Sciences (Washington: National Academy Press, 1996).

International Organization for Standardization 10993: Biological Evaluation of Medical Devices, Part 10: Tests for Irritation and Sensitization.

OLAW, Public Health Service Policy on Humane Care and Use of Laboratory Animals.

United States Code of Federal Regulation (CFR) 9: The Animal Welfare Act.

United States Pharmacopeia (USP), current edition.

Example 9

USP and Iso Systemic Toxicity Study Extract

Purpose:

The objective of this study is to evaluate acute systemic toxicity of leachables extracted from the test article following a single intravenous or intraperitoneal injection in mice. This study will be conducted in accordance with the methods recommended by the International Organization for Standardization 10993: Biological Evaluation of Medical Devices, Part II: Tests for Systemic Toxicity.

Test Article:

The sample will be prepared as follows:
1. Ratio of Test Article to Extraction Vehicle:
    Material thickness less than 0.5 mm—ratio of 120 cm$^2$:20 ml
    Material thickness greater than or equal to 0.5 mm ratio of 60 cm$^2$:20 ml
    Irregularly shaped objects and/or sponsor option—ratio of 4 g:20 ml
2. Extraction Vehicles:
    0.9% sodium chloride USP solution (SC)
    alcohol in saline 1:20 solution (AS)
    polyethylene glycol 400 (PEG)*
    vegetable oil
Note: Due to the known pH of these vehicles, the pH of the test article extracts will not be determined.
    *If PEG is used, the PEG test extract and reagent control will be diluted with saline to obtain 200 mg of PEG/ml.
3. Extraction Conditions:
    121° C., 1 hour
    70° C., 24 hours 50° C., 72 hours
    37° C., 72 hours Control Article:

Blank controls (extraction vehicle without test material) will be prepared in the same way and at the same time as the test extracts.

Test System:

| | |
|---|---|
| Species: | Mouse (*Mus musculus*) |
| Strain: | Outbred albino |
| Source: | approved supplier |
| Sex: | No particular gender is prescribed for this test |
| Body Weight Range: | 17-23 grams at injection |
| Age: | No particular age is prescribed for this test |
| Acclimation Period: | Minimum 1 day |
| Number of Animals: | Five per extract and control |
| Identification Method: | Ear punch |

Justification of Test System:

Mice have historically been used to evaluate biomaterial extracts. The use of albino mice injected with a single intravenous (iV) or intraperitoneal (IP) dose of test article extract or control blank have been suggested by the current USP and ISO for evaluation of medical plastics.

Methods and Route of Administration:

Prior to dosing, the mice will be identified and weighed. Five animals will each be injected with the appropriate test extract at a dose of 50 ml/kg (SC, AS, vegetable oil) or 10 g/kg (PEG). Five mice will be similarly injected with the corresponding extraction vehicles. The SC and AS will be injected intravenously via the lateral tail vein while the PEG and vegetable oil will be injected intraperitoneally.

Mice will be observed for adverse reactions immediately after dosing, and at 4, 24, 48 and 72 hours after injection. Following the 72 hour observation, the animals will be weighed. Any animal found dead will be subjected to a gross necropsy of the viscera. After the test is completed, all animals will be handled in accordance with approved procedures.

Evaluations and Statistics:

No statistical analysis of the data will be performed. If during the observation period none of the mice treated with the test extract show a significantly greater reaction than the corresponding control mice, then the test sample meets the test requirements. If two or more mice die, or if abnormal behavior such as convulsions or prostration occurs in two or more mice, or if body weight loss greater than 2 grams occurs in three or more mice, the test sample does not meet the test requirements.

If any mice treated with the test extract show only slight signs of toxicity and not more than one mouse shows gross signs of toxicity or dies, a ten mouse retest may be required. If all ten mice treated with the test extract on the repeat test show no significant reaction greater than the control mice, then the test sample meets the current test requirements.

Report:

The final report will include a description of the methods employed, individual body weights, and any observations.

Records:

Test article preparation, dates of relevant activities (such as the study initiation and completion), initial and final body weights, and observations will be recorded.

References for Example 9:

21 CFR 58 (GLP Regulations).

*Guide for the Care and Use of Laboratory Animals*, Institute for Laboratory Animal Research, National Academy of Sciences (Washington: National Academy Press, 1996).

International Organization for Standardization 10993: Biological Evaluation of Medical Devices, Part 11: Tests for Systemic Toxicity.
OLAW, Public Health Service Policy on Humane Care and Use of Laboratory Animals (NIH Publication).
United States Pharmacopeia (USP), current edition.

Example 10

Rat Subchronic Intravenous Toxicity Study

Purpose:
The objective of this study is to evaluate the subchronic systemic toxicity of leachables extracted from the test article following repeated intravenous injections in rats for a period of 14 consecutive days.
Test Article:
1. Ratio of Test Article to Extraction Vehicle:
   Material thickness less than 0.5 mm—ratio of 120 $cm^2$:20 ml
   Material thickness greater than or equal to 0.5 mm—ratio of 60 $cm^2$:20 ml
   Irregularly shaped objects and/or sponsor option—ratio of 4 g:20 ml
2. Extraction Conditions:
   121° C., 1 hour
   70° C., 24 hours
   50° C., 72 hours
   The extracts will be used within 24 hours of completion of the extraction process or as directed by the sponsor.
Control Article:
A vehicle control (SC without test article) will be prepared in the same way and at the same time as the test extract. A single group of common control animals may be dosed when multiple test articles are evaluated at the same time.
Test System:

| | |
|---|---|
| Species: | Rat (*Rat us norvigicus*) |
| Strain: | Hla ®: (SD)CVF ® |
| Source: | Hilltop Lab Animals, Inc. |
| Sex: | Ten male, ten female |
| Body Weight Range: | No particular weight range is prescribed for this study, however, individual pretreatment body weights will be within 20% of the group mean for each sex |
| Age: | Approximately 6 to 8 weeks old at first treatment |
| Acclimation Period: | Minimum 5 days |
| Number of Animals: | Twenty |
| Identification Method: | Ear punch or tag |

Methods and Route of Administration:
No more than one day prior to the first dose, rats will be weighed and randomly assigned to each treatment group. Ten rats (five male, five female) will receive an injection of the test article extract once each day for 14 consecutive days. The test extract will be injected via the lateral tail vein at a dose of 10.0 ml/kg. The individual daily dose will be based on the weight of each animal on the first dose day of each week. The appropriate dose volume will be calculated to the nearest 0.1 ml. An appropriate gauge needle attached to a disposable syringe will be used to deliver the injection. The injection rate will be approximately 1.0 ml/10 seconds. Animals will be dosed at approximately the same time each day. Ten rats (five male, five female) will be similarly injected with the control blank. The first day of dosing will be designated as day 1.
Laboratory Observations:
1. Animals will be observed daily for general health. Rats will also be observed for any adverse reactions immediately after injection.
2. Detailed examinations for clinical signs of disease or abnormality will be conducted at randomization and on days 8 and 15.
3. Body weights will be recorded to the nearest whole gram prior to the first dose, on day 8, 14 (pre-fasted weight) and 15 (fasted weight).
4. In the event of mortality, the following contingencies will apply:
   a. Should any animal die during the study, a macroscopic examination of the viscera will be conducted. Because of rapid postmortem tissue changes in small rodents, no final body weight or blood collection will be attempted. The organs and tissues designated in the Terminal Procedures portion of this protocol will be collected and fixed for histopathologic evaluation. The number of days the animal was on test will be considered in the final evaluation.
   b. Should any animal exhibit adverse clinical signs or suffer from cage injury that for humane reasons necessitates euthanasia, it will be subject to the Terminal Procedures. The number of days the animal was on test will be considered in the final evaluation.

Terminal Procedures:
At the end of the workday on day 14, the animals will be weighed and food will be withheld for a maximum of 20 hours. On day 15, the animals will be weighed and then anesthetized by intraperitoneal injection of ketamine hydrochloride and xylazine (88 mg/kg+12 mg/kg) dosed at 3.0 ml/kg. The abdomen will be opened and a blood specimen will be collected from the posterior vena cava. The blood specimens will be forwarded to a contract laboratory for complete blood cell count with differential and clinical chemistry analyses. Rats will be euthanized by exsanguination while anesthetized.

Following exsanguination, a macroscopic observation of the viscera will be conducted. The following organs will be removed: heart, lungs, liver, spleen, thymus, kidneys (2), adrenal glands (2), mesenteric lymph nodes, submandibular lymph nodes, gonads (2) and any tissue with visible gross lesions. The liver, spleen, thyrnus, kidneys, adrenal glands and gonads will be weighed. Paired organs will be weighed together. The tissues will be preserved in 10% neutral buffered formalin (NBF) until further processing. The carcasses will be discarded.

After fixation, the tissues will be histologically processed (embedded, sectioned and stained in hematoxylin and eosin) for microscopic evaluation by a qualified pathologist.
Evaluation and Statistics:
Body weight data, organ weight data, organ/body weight ratios, hematology and clinical chemistry data will be evaluated statistically. Pre-fasted body weights will be used to determine weight gain and the fasted body weights will be used to determine anesthetic dosages at termination and organ/body weight ratios. Descriptive statistics and group comparisons of data will be accomplished using a validated statistical software package. After screening the data for normality and equal variance, the appropriate parametric or nonparametric tests will be performed. Normally distributed data with equal variance will be considered parametric and evaluated using an "unpaired t-test" for comparison of two groups. Jf data is nonparametric, the "Mann-Whitney Rank Sum Test" is used for two group comparisons. The data to be analyzed will include: body weight, organ weight and hematological parameters. The treatment groups will be used as variables. Calculations resulting in probability (p) values less than 0.05 will be considered statistically significant. If directed by the evaluating pathologist, statistical evaluation of pathologic findings may be conducted.

Clinical signs of systemic illness or death will not be analyzed statistically unless a rationale (such as frequently observed clinical signs or emergence of a pattern) for such analysis is apparent from these data. If the incidence of occurrence of any one or more observations is sufficient to warrant analysis, a chisquare test will be employed.

Data from male and female rats for body weights will be analyzed separately until and unless a rationale exists for combining the sexes. Body weight data will be expressed as absolute values. Data from male and female rats for hematology parameters will be analyzed separately unless a rationale exists for combining the sexes. In the event of statistical significance for any hematologic parameter, the results will be compared to a reference range to aid in determining biological significance.

Report:

The final report will include a description of the methods employed, clinical observations, body weight data, hematology and clinical chemistry data, organ weight data, organ/body weight ratios, necropsy findings, the microscopic evaluation in the histopathology report, the statistical analyses and conclusions.

References for Example 10:

21 CFR 58 (GLP Regulations).

Guide for the Care and Use of Laboratory Animals, Institute for Laboratory Animal Research, National Academy of Sciences (Washington: National Academy Press, 1996).

ISO 10993-11. Biological Evaluation of Medical Devices, Part 11: Tests for Systemic Toxicity.

OECD Guideline for Testing of Chemicals, Repeated Dose Oral Toxicity—Rodent: 28-day or 14-day Study, Document Number 407.

OLAW, Public Health Service Policy on Humane Care and use of Laboratory Animals (NIH Publication).

Example 11

Genotoxicity

Bacterial Reverse Mutation Study

Purpose of the Study:

The purpose of the study is to evaluate whether an extract of the test material or a solubilized material will cause mutagenic changes in a tryptophan-dependent strain of *Escherichia coli* or in one or more strains of histidine-dependent *Salmonella typhimurium* in the presence or absence of 59 metabolic activation. The Bacterial Reverse Mutation Study will be used as a rapid screening procedure for the determination of inutagenic and potential carcinogenic hazards and should be used in conjunction with other tests that characterize potential genotoxicity properties. This study will be based on OECD guidelines and the requirements of the International Organization for Standardization: Biological Evaluation of Medical Devices—Part 3: Tests for Genotoxicity, Carcinogenicity and Reproductive Toxicity.

Test Article:

The sample will be prepared as follows:

Test article form:
  Soluble material (solid or liquid)—complete "Preparation of Soluble Material"
  Insoluble material—complete "Preparation of Extract"

Preparation of Extract (for Insoluble Materials):

1. Ratio of Test Material to Vehicle:
  Material thickness less than 0.5 mm, use ratio of 120 cm$^2$: 20 ml
  Material thickness greater than or equal to 0.5 nun, use ratio of 60 cm$^2$:20 ml
  Irregularly shaped objects and/or sponsor option, use ratio of 4 g:20 ml 2. Vehicle:
  0.9% Sodium Chloride for Injection, USP
  Dimethyl sulfoxide (DMSO)*
  95% ethanol (EtOH)**
    *Dimethyl sulfoxide can be extracted at 37° C. for 72 hours, 70° C. for 24 hours or 50° C. for 72 hours.
    **95% ethanol can only be extracted at room temperature (various times can be used).

3. Conditions (Use Highest Temperature that Will not Degrade material);
  121° C., 1 hour
  70° C., 24 hours
  50° C., 72 hours
  37° C., 24 hours
  room temperature, 72 hours Preparation of Soluble Material:

1. —Solid:
  One gram of the sample will be transferred to a 10 ml volumetric flask. Various sized flasks may be used to accommodate nature of test material utilizing 100 mg/ml or 10% w/v. Appropriate vehicle (specified below) will be added (q.s.) to the 10 ml (or appropriate) demarcation to achieve 100 mg/ml or a 10% (w/v) solution of the material.

2. —Liquid:
  One milliliter of the sample will be transferred to a 10 ml volumetric flask. Various sized flasks may be used to accommodate nature of test material utilizing 100 mg/ml or 10% v/v. Appropriate vehicle (specified below) will be added (q.s.) to the 10 ml (or appropriate) demarcation to achieve 100 mg/ml or a 10% (v/v) solution of the material.
  NOTE: GLP regulations 21 CFR 58.113 requires concentration analysis and stability determination for mixtures with carriers.

Vehicles:
  0.9% Sodium Chloride for Injection, USP
  Dimethyl sulfoxide (DMSO)
  95% ethanol (EtOH)
  All preparations of soluble materials will be performed the day of test. In the event the material does not completely dissolve at these concentrations, serial dilutions will be prepared. The highest possible concentration that achieves complete dissolution of the material will be used for testing purposes.

Test System:

Each *S. typhimurium* tester strain contains a specific mutation in the histidine operon and other mutations that increase their ability to detect mutagens. The *E. coli* strain contains a mutation in the tryptophan operon and a deletion in the uvrA gene. These genetically altered *S. typhimurium* strains (TA9S, TA100, TA1535, and TA1537) and *E. coli* strain (WP2uvrA) cannot grow in the absence of histidine or tryptophan, respectively. When placed in a histidine-free (for *S. typhimurium*) or tryptophan-free (for *E. coli*) medium, only those cells which mutate spontaneously back to their wild type state (histidine independent by manufacturing their own histidine, or tryptophan independent by manufacturing their own iryptophan) are able to form colonies. The spontaneous mutation rate (or reversion rate) for any one strain is relatively constant, but if a mutagen is added to the test system, the mutation rate is significantly increased.

| Tester Strain | Mutations/Genotypic Relevance |
| --- | --- |
| *S. typhimurium* TA98 | hisD3O52, rfa, uvrB, frameshift, pKM101 |
| *S. typhimurium* TA 100 | hisG46, rfa, uvrB, missense, pKM101 |
| *S. typhimurium* TA 1535 | hisG46, rfa, uvrB, missense |
| *S. typhimurium* TA 1537 | hisC3O76, rfa, uvrB, frameshift |
| *E. coli* WP2uvrA | trpE65, uvrA, missense | rfa = causes partial loss of the lipopolysaccharide wall which increases permeability of the cell to large molecules (i.e., crystal violet inhibition)
uvrB or uvrA = deficient DNA excision - repair system (i.e., ultraviolet sensitivity)
frameshift = base-pair addition/deletion
missense = base-pair substitution
pKM101 = plasmid confers ampicillin resistance (R-factor) and enhances sensitivity to mutagens Metabolic Activation:

Aroclor 1254-induced rat liver (s9 homogenate) will be used as metabolic activation. The material is prepared from male, Sprague Dawley rats. The rats are induced with one intraperitoneal injection of Aroclor 1254 (500 mg/ml) 5 days prior to sacrifice. The S9 homogenate is purchased from Organon Teknika Corporation, Box 15969, Durham, N.C. 27704-0969. Just prior to use, the S9 homogenate will be mixed with a buffer containing 0.4 M $MgCl_2$/65 M KCl, 1.0 M Glucose-6-phosphate, 0.1 M NADP, 0.2 M sodium phosphate buffer and sterile water.

Preparation of Tester Strains:

Cultures of *Salmonella typhimurium*, TA98, TA100, TA1535 and TA1537, and *Escherichia coli*, WP2uvrA, will be inoculated to individual Erlenmeyer flasks containing oxoid broth. The inoculated broth cultures will be incubated at 37±2° C. in an incubator shaker operating at 115-125 rpm for 10-12 hours.

Preparation of Negative Control:

Negative control (vehicle without test material) will be utilized for each tester strain with and without S9 activation.

Preparation of Positive Controls:

A known mutagen, Dexon (paradimethylaminobenzene diazosulfonic acid sodium salt), will be used as a positive control to demonstrate that tester strains TA98, TA100, and TA1537 are sensitive to mutation to the wild type state. For tester strain TA 1535, sodium azide will be used as a positive control. For tester strain TA100, 2-aminofluorene will be used as a positive control. For tester strain WP2uvrA, 2-aminoanthracene and methylmethane-sulfonate will be used as positive controls. Although metabolic activation is only required with 2-aminofluorene and 2-aminoanthracene to induce mutagenic results, all positive controls will be tested with and without S9 homogenate.

Strain Characteristics and Strain Standard Plate Counts:

Strain characteristics will be verified and viable counts will be determined.

Spot Plate Inhibition Screen:

The extract(s) or solubilized material(s) and negative control(s) will be evaluated by a spot plate technique modeled after the antimicrobial zone of inhibition test. This screen is used to evaluate extract or solution concentrations for toxicity which are noninhibitory to the *Salmonella* strains and the *E. coli* strain.

Separate tubes containing 2 ml of molten top agar supplemented with histidine-biotin (for *S. typhimurium*) or with tryptophan (for *E. coli*) will be inoculated with 0.1 ml of culture for each of the five tester strains. After mixing, the agar will be poured across the surface of separate Minimal E plates labeled with lab number, appropriate tester strain, and dose level (when necessary). Once the agar solidifies, sterile filter discs will be placed in the center of the plates. A 0.1 ml aliquot of the extract or solubilized material will be added to the filter discs on each of the labeled plates. Parallel testing will be conducted with a negative control. To demonstrate a positive zone of inhibition, lOX stock Dexon will be used.

The plates will be incubated at 37±2° C. for 2-3 days. Following the incubation period, the zone of growth inhibition will be recorded. If significant inhibition of the background lawn occurs, the extract or solubilized material concentration will be adjusted by preparing one or more dilutions and repeating the inhibition screen to find a nontoxic level.

Standard Plate Incorporation Assay:

Separate tubes containing 2 ml of molten top agar supplemented with histidine-biotin solution (for *S. typhimurium*) or tryptophan (for *E. coli*) will be inoculated with 0.1 ml of culture for each of the five tester strains, and 0.1 ml of the test material. A 0.5 ml aliquot of SWI or S9 homogenate, simulating metabolic activation, will be added when necessary. The mixture will be poured across triplicate Minimal B plates labeled with lab number, appropriate tester strain, and S9 metabolic activation (when applicable). Parallel testing will be conducted on a negative control and five positive controls.

Histidine-free media plates (for *S. typhimurium*) and tryptophan-free media plates (for *E. coli*) will be prepared in triplicate as follows:

1. Extract or solubilized material with and without S9 activation
2. Negative control with and without S9 activation
3. 1× Dexon (known mutagen) with and without S9 activation with strains TA9S, TA100, and TA1 537
4. 1×2-aminofluorene (known mutagen) with and without S9 activation with strain TA 100
5. 1× Sodium azide (known mutagen) with and without S9 activation with strain TA1535
6. 1×2-aminoanthracene (known mutagen) with and without S9 activation with strain WP2uvrA
7. 1× Methylmethane-sulfonate (known mutagen) with and without S9 activation with strain WP2uvrA The plates will be incubated at 37±2° C. for 2-3 days. After the incubation period, the revertant colonies on each plate (test, negative and positive) will be counted and recorded. The mean number of revertants will be calculated.

Evaluation of Test Results:

The mean number of revertants of the triplicate test plates will be compared to the mean number of revertants of the triplicate negative control plates for each of the five tester strains employed. The means obtained for the positive controls are used as points of reference. For a test material to be identified as a test failure or "potential mutagen" there must be a 2-fold or greater increase in the number of mean revertants over the means obtained from the negative control, for any/all five tester strains. If no 2-fold increase is present, the test material is considered nonmutagenic.

Any apparent "positive response" will be confirmed by demonstrating a dose-response relationship using three nontoxic dose levels of the test material. There should be a range of concentrations that produce a linear dose response. In the event linearity cannot be established, the assay will be repeated with an appropriate change in dose levels. A test material will be judged mutagenic if it causes a dose-related increase in the number of revertants over a minimum of two increasing dose concentrations.

Test Validity:

For any assay to be considered valid, it must meet the following criteria:

1. Strain characteristics: All *S. typhimurium* tester strains (TA98, TA100, TA1535, and TA1537) must exhibit sensitivity to crystal violet (rfa mutation), and ultraviolet light (uvrB), and must exhibit no growth on biotin plates, and growth on histidine-biotin plates. Tester strains TA98 and TA 100 must exhibit resistance to ampicillin (R-factor); tester strains TA1535 and TA1537 must exhibit sensitivity to ampicillin. Tester strain WP2uvrA must exhibit sensitivity to ultraviolet light, no growth on tryptophan deficient plates, growth on tryptophan supplemented media and sensitivity to ampicillin.
2. Strain Standard Plate Counts: A viable count on the working culture suspensions for each tester strain (TA98, TA100, TA1535, TA1537 and WP2uvrA) should not be less than 1×10 CFU/ml.
3. Spot Plate Inhibition Screen: Each prepared extract or solubilized material will be evaluated for inhibition or toxicity to the cells. A test sample that is noninhibitory to moderately noninhibitory to the tester strains will be tested by the standard plate incorporation method. In the event a test material is inhibitory, dilutions will be required to find a nontoxic level.
4. Standard Plate Incorporation Assay: Each positive control mean must exhibit at least a 3-fold increase over the respective negative control mean of the *Salmonella* tester strain employed, and at least a 2-fold increase over the respective negative control mean of the *E. coli* tester strain. Exceptions include conditions not intended to provoke a mutagenic response (e.g. 2-aminoanthracene and 2-aminofluorene without metabolic activation). The negative control results of each tester strain will exhibit a characteristic number of spontaneous revertants. Spontaneous reversion rates may vary, but should be consistent with the ranges specified (see Table below). The Table is meant as a guideline only. Negative control results for tester strains may fall outside of the range listed. In such an instance, the results should be evaluated with caution.

| Species | Tester Strain | Number of Spontaneous Revertants |
|---|---|---|
| *S. typhimurium* | TA98 | 15-50 |
| | TA100 | 120-240 |
| | TA1537 | 3-28 |
| | TA1535 | 10-35 |
| *E. coli* | WP2uvrA | 20-125 |

References for Example 11:

Ames, B. N., McCann, 3., and Yamasaki, E., "Methods for Detecting Carcinogens and Mutagens with the *Salmonella*/Mammalian-Microsome Mutagenicity Test" Mutation Research 31, (1975): 347-364.

Brusick, D. J., V. F. Simmon, H. S. Rosenlcranz, V. A. Ray, and K S. Stafford, "An Evaluation of the *Escherichia coli* WP2 and WP2uvrA Reverse Mutation Assay," Mutation Research 76, (1980): 169-190.

Maron, Dorothy M., Ames, Bruce N., "Revised Methods for the *Salmonella* Mutagenicity Test," Mutation Research, 113 (1983): 175-215.

ISO 10993-3. Biological Evaluation of Medical Devices, Part 3: Tests for Genotoxicity, Carcinogenicity and Reproductive Toxicity.

OECD Guideline for the Testing of Chemicals, Proposal for Replacement of Guidelines 471 Bacterial Reverse Mutation Test, Document Number 471.

Ortiz, A. J., M. T. Pollastrini, M. Barea, and D. Ordóhez, "Bacterial Mutagenic Evaluation of Luxabendazole, a New Broad Spectrum Antihelminic, with the *Salmonella typhimurium* Histidine and the *Escherichia coli* Tryptophan Reversions Tests," Mutagenesis 11 (1996): 27-31.

Test validation, Bacterial Mutagenicity Test: NAMSA lab number 98T-00785-00.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A chemical gel comprising at least one silicon-containing biostable polymer having monomers with an average functionality in the range of from 2.05 to 3.5 in which the biostable polymer is a polyurethane or polyurethane urea which is a reaction product of:

(a) at least one silicon-containing polyol or polyamine having 2 or more functional groups in which the silicon-containing polyol or polyamine is a compound of formula (II)

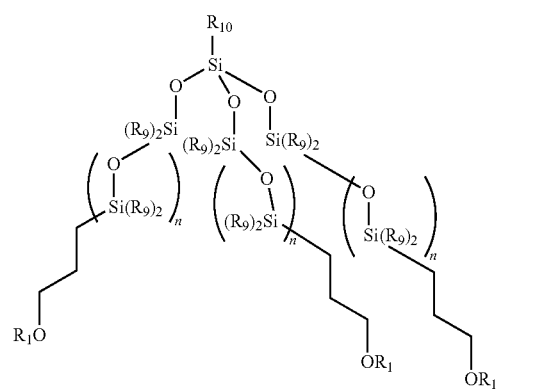

in which $R_1$ is selected from $C_{1-6}$ alkylene optionally substituted with OH or NR'R" in which R' and R" are independently selected from H, $CO_2H$ and $C_{1-6}$ alkyl;

$R_9$ is $C_{1-4}$ alkyl;

$R_{10}$ is optionally substituted $C_{1-4}$ alkyl or

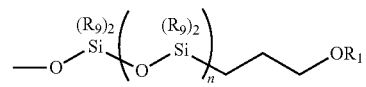

in which $R_1$ and $R_9$ are as defined above;

x is 5 to 30;

y is 1 to 10; and n is 1 to 10;

(b) a polyisocyanate; and
(c) at least one non-silicon containing compound selected from a polycarbonate or a $C_{1-6}$ alkane having 1 or more functional groups selected from OH, NR'R" in which R' and R" are the same or different and selected from H, $CO_2H$ and $C_{1-6}$ alkyl; wherein the gel has an NCO/OH or $NH_2$ ratio less than 1.

2. A gel according to claim 1 in which the average functionality is from 2.1 to 3.25.

3. A gel according to claim 1 in which the compound of formula (II) is as follows:

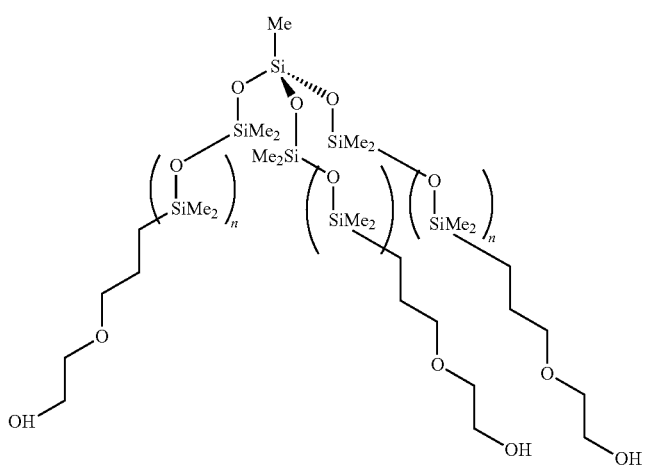

(IIa)

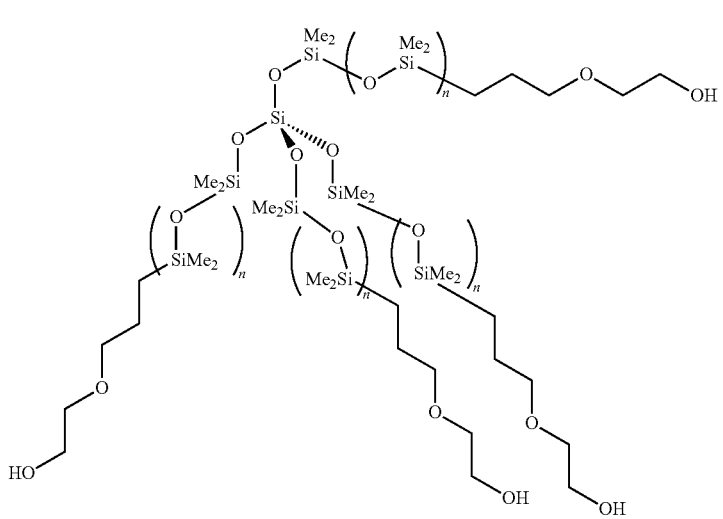

(IIb)

in which n is as defined in claim 1, wherein the molecular weight of the compound of formula (IIa) or (IIb) is from 1000-5000.

4. A gel according to claim 1 in which the polyisocyanate (b) is polymeric 4,4'-diphenylmethane diisocyanate (MDI), methylene biscyclohexyl diisocyanate ($H_{12}$MDI), p-phenylene diisocyanate (p-PDI), trans-cyclohexane-1,4-diisocyanate (CHDI), 1,6-diisocyanatohexane (DICH), 1,5-diisocyanatonaphthalene (NDI), para-tetramethylxylenediisocyanate (p-TMXDI), meta-tetramethylxylene diisocyanate (m-TMXDI), 2,4-toluene diisocyanate (2,4-TDI) isomers or mixtures thereof or isophorone diisocyanate (IPDI).

5. A gel according to claim 1 in which the polycarbonate is a poly(alkylene carbonate); a polycarbonate prepared by reacting alkylene carbonate with alkanediol or a silicon based polycarbonate prepared by reacting alkylene carbonate with 1,3-bis(4-hydroxybutyl)-1,1,3,3-tetramethyldisiloxane (BHTD) and/or alkanediol.

6. A gel according to claim 1 in which the $C_{1-6}$ alkane having 1 or more functional groups is methane diol, butane diol or hexane diol.

7. A gel according to claim 1 in which the NCO/OH or $NH_2$ ratio is from 0.4 to 0.7.

8. A gel according to claim 1 having less than 35% extractables.

* * * * *